US008647861B2

(12) United States Patent
Ingber et al.

(10) Patent No.: US 8,647,861 B2
(45) Date of Patent: Feb. 11, 2014

(54) ORGAN MIMIC DEVICE WITH MICROCHANNELS AND METHODS OF USE AND MANUFACTURING THEREOF

(75) Inventors: Donald E. Ingber, Boston, MA (US); Dongeun Huh, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 13/054,095

(22) PCT Filed: Jul. 16, 2009

(86) PCT No.: PCT/US2009/050830
§ 371 (c)(1),
(2), (4) Date: Jun. 30, 2011

(87) PCT Pub. No.: WO2010/009307
PCT Pub. Date: Jan. 21, 2010

(65) Prior Publication Data
US 2011/0250585 A1    Oct. 13, 2011

Related U.S. Application Data

(60) Provisional application No. 61/081,080, filed on Jul. 16, 2008.

(51) Int. Cl.
*C12M 1/00* (2006.01)

(52) U.S. Cl.
USPC ............. 435/289.1; 435/283.1; 435/288.5; 435/297.1; 435/325; 435/371; 506/10

(58) Field of Classification Search
None
See application file for complete search history.

(56) References Cited

U.S. PATENT DOCUMENTS

| 3,300,386 A | 1/1967 | Aron-Brunetiere et al. |
| 3,313,290 A | 4/1967 | Chance et al. |
| 3,722,504 A | 3/1973 | Sawyer |

(Continued)

FOREIGN PATENT DOCUMENTS

| DE | 2431918 | 1/1976 |
| EA | 008075 B1 | 2/2007 |

(Continued)

OTHER PUBLICATIONS

Kim et al., Sensors and Actuators B: Chemical, 128:108-116 (2007). "Microfluidic biomechanical device for compressive cell stimulation and lysis."

(Continued)

*Primary Examiner* — Lora E Barnhart Driscoll
*Assistant Examiner* — Stephanie McNeil
(74) *Attorney, Agent, or Firm* — Nixon Peabody LLP

(57) ABSTRACT

System and method includes a body having a central microchannel separated by one or more porous membranes. The membranes are configured to divide the central microchannel into a two or more parallel central microchannels, wherein one or more first fluids are applied through the first central microchannel and one or more second fluids are applied through the second or more central microchannels. The surfaces of each porous membrane can be coated with cell adhesive molecules to support the attachment of cells and promote their organization into tissues on the upper and lower surface of the membrane. The pores may be large enough to only permit exchange of gases and small chemicals, or to permit migration and transchannel passage of large proteins and whole living cells. Fluid pressure, flow and channel geometry also may be varied to apply a desired mechanical force to one or both tissue layers.

21 Claims, 11 Drawing Sheets

(56) References Cited

U.S. PATENT DOCUMENTS

| | | |
|---|---|---|
| 3,941,662 A | 3/1976 | Munder et al. |
| 3,948,732 A | 4/1976 | Haddad et al. |
| 4,225,671 A | 9/1980 | Puchinger et al. |
| 4,436,824 A | 3/1984 | Bishop |
| 4,446,229 A | 5/1984 | Indech |
| 4,537,860 A | 8/1985 | Tolbert et al. |
| 4,610,878 A | 9/1986 | Wilson et al. |
| 4,629,686 A | 12/1986 | Gruenberg |
| 4,650,766 A | 3/1987 | Harm et al. |
| 4,673,650 A | 6/1987 | Braden |
| 4,720,462 A | 1/1988 | Rosenson |
| 4,734,372 A | 3/1988 | Rotman |
| 4,737,455 A | 4/1988 | De Baetselier |
| 4,749,654 A | 6/1988 | Karrer et al. |
| 4,835,102 A | 5/1989 | Bell et al. |
| 4,839,280 A | 6/1989 | Banes |
| 4,851,354 A | 7/1989 | Winston et al. |
| 4,929,542 A | 5/1990 | Risley |
| 4,940,853 A | 7/1990 | Vandenburgh |
| 5,002,890 A | 3/1991 | Morrison |
| 5,043,260 A | 8/1991 | Jauregui |
| 5,108,926 A | 4/1992 | Klebe |
| 5,160,490 A | 11/1992 | Naughton et al. |
| 5,217,899 A | 6/1993 | Shapiro et al. |
| 5,290,684 A | 3/1994 | Kelly |
| 5,316,905 A | 5/1994 | Mori et al. |
| 5,348,879 A | 9/1994 | Shapiro et al. |
| 5,486,335 A | 1/1996 | Wilding et al. |
| 5,496,697 A | 3/1996 | Parce et al. |
| 5,498,392 A | 3/1996 | Wilding et al. |
| 5,587,128 A | 12/1996 | Wilding et al. |
| 5,612,188 A | 3/1997 | Shuler et al. |
| 5,637,469 A | 6/1997 | Wilding et al. |
| 5,726,026 A | 3/1998 | Wilding et al. |
| 5,744,366 A | 4/1998 | Kricka et al. |
| 5,750,329 A | 5/1998 | Quinn et al. |
| 5,820,769 A | 10/1998 | Chou |
| 5,900,160 A | 5/1999 | Whitesides et al. |
| 5,906,828 A | 5/1999 | Cima et al. |
| 6,048,723 A | 4/2000 | Banes |
| 6,054,277 A | 4/2000 | Furcht et al. |
| 6,133,030 A | 10/2000 | Bhatia et al. |
| 6,197,575 B1 | 3/2001 | Griffith et al. |
| 6,255,106 B1 | 7/2001 | Marx et al. |
| 6,306,644 B1 | 10/2001 | Marx et al. |
| 6,329,195 B1 | 12/2001 | Pfaller |
| 6,454,924 B2 | 9/2002 | Jedrzejewski et al. |
| 6,472,202 B1 | 10/2002 | Banes |
| 6,530,370 B1 | 3/2003 | Heinonen |
| 6,562,616 B1 | 5/2003 | Toner et al. |
| 6,586,235 B1 | 7/2003 | Banes |
| 6,630,801 B2 | 10/2003 | Schuurmans |
| 6,645,432 B1 | 11/2003 | Anderson et al. |
| 6,645,759 B2 | 11/2003 | Banes |
| 6,653,124 B1 | 11/2003 | Freeman |
| 6,730,516 B2 | 5/2004 | Jedrzejewski et al. |
| 6,921,253 B2 | 7/2005 | Shuler et al. |
| 6,998,265 B2 | 2/2006 | Banes |
| 7,049,057 B2 | 5/2006 | Atala et al. |
| 7,288,405 B2 | 10/2007 | Shuler et al. |
| 7,314,718 B1 | 1/2008 | Dasgupta et al. |
| 7,438,856 B2 | 10/2008 | Jedrzejewski et al. |
| 7,745,209 B2 | 6/2010 | Martin et al. |
| 7,763,456 B2 | 7/2010 | Li et al. |
| 7,790,028 B1 | 9/2010 | Weinberg et al. |
| 7,960,166 B2 | 6/2011 | Vacanti et al. |
| 7,964,078 B2 | 6/2011 | Lee et al. |
| 7,976,795 B2 | 7/2011 | Zhou et al. |
| 7,977,089 B2 | 7/2011 | Wikswo et al. |
| 7,985,336 B2 | 7/2011 | Weinberg et al. |
| 8,030,061 B2 | 10/2011 | Shuler et al. |
| 8,147,562 B2 | 4/2012 | Vacanti et al. |
| 8,187,863 B2 | 5/2012 | Sim et al. |
| 8,268,152 B2 | 9/2012 | Stelzle et al. |
| 8,273,572 B2 | 9/2012 | Martin et al. |
| 8,318,479 B2 | 11/2012 | Domansky et al. |
| 8,343,740 B2 | 1/2013 | Gonda et al. |
| 8,357,528 B2 | 1/2013 | Vacanti et al. |
| 8,460,546 B2 | 6/2013 | Weinberg et al. |
| 8,470,589 B2 | 6/2013 | Martin et al. |
| 2002/0129813 A1 | 9/2002 | Litherland et al. |
| 2002/0173033 A1 | 11/2002 | Hammerick et al. |
| 2003/0021792 A1 | 1/2003 | Roben et al. |
| 2003/0082795 A1 | 5/2003 | Shuler et al. |
| 2003/0096405 A1 | 5/2003 | Takayama et al. |
| 2003/0175824 A1 | 9/2003 | Pishko et al. |
| 2004/0034435 A1 | 2/2004 | Atala |
| 2004/0132166 A1 | 7/2004 | Miller et al. |
| 2005/0032205 A1 | 2/2005 | Smith et al. |
| 2005/0169962 A1 | 8/2005 | Bhatia et al. |
| 2005/0266393 A1 | 12/2005 | Baxter et al. |
| 2005/0273995 A1 | 12/2005 | Kanagasabapathi et al. |
| 2006/0019326 A1 | 1/2006 | Vacanti et al. |
| 2006/0099116 A1 | 5/2006 | Manger et al. |
| 2006/0154361 A1 | 7/2006 | Wikswo et al. |
| 2006/0263336 A1 | 11/2006 | Caplan |
| 2006/0270023 A1 | 11/2006 | LeDuc et al. |
| 2007/0015273 A1 | 1/2007 | Shuler et al. |
| 2007/0015274 A1 | 1/2007 | Shuler et al. |
| 2007/0015275 A1 | 1/2007 | Shuler et al. |
| 2007/0020693 A1 | 1/2007 | Shuler et al. |
| 2007/0026519 A1 | 2/2007 | Shuler et al. |
| 2007/0037273 A1 | 2/2007 | Shuler et al. |
| 2007/0037275 A1 | 2/2007 | Shuler et al. |
| 2007/0037277 A1 | 2/2007 | Shuler et al. |
| 2007/0048727 A1 | 3/2007 | Shuler et al. |
| 2007/0122794 A1 | 5/2007 | Shuler et al. |
| 2007/0122896 A1 | 5/2007 | Shuler et al. |
| 2007/0144514 A1 | 6/2007 | Yeates et al. |
| 2007/0172943 A1 | 7/2007 | Freedman et al. |
| 2007/0207194 A1 | 9/2007 | Grayburn et al. |
| 2007/0224677 A1 | 9/2007 | Neumann |
| 2007/0243627 A1 | 10/2007 | Takayama et al. |
| 2007/0275435 A1 | 11/2007 | Kim et al. |
| 2007/0275455 A1 | 11/2007 | Hung et al. |
| 2007/0275882 A1 | 11/2007 | Meijer et al. |
| 2007/0281353 A1 | 12/2007 | Vacanti et al. |
| 2008/0032380 A1 | 2/2008 | Kleis et al. |
| 2008/0064088 A1 | 3/2008 | Shuler et al. |
| 2008/0166794 A1 | 7/2008 | Shuler et al. |
| 2008/0166795 A1 | 7/2008 | Shuler et al. |
| 2008/0233607 A1 | 9/2008 | Yu et al. |
| 2008/0318334 A1 | 12/2008 | Robotti |
| 2009/0028755 A1 | 1/2009 | Jedrzejewski et al. |
| 2009/0074623 A1 | 3/2009 | Park et al. |
| 2009/0078614 A1 | 3/2009 | Varghese et al. |
| 2009/0131858 A1 | 5/2009 | Fissell et al. |
| 2009/0134235 A1 | 5/2009 | Ivri |
| 2009/0220932 A1 | 9/2009 | Ingber et al. |
| 2010/0041128 A1 | 2/2010 | Banes et al. |
| 2010/0043494 A1 | 2/2010 | Gascon et al. |
| 2010/0267136 A1 | 10/2010 | Vacanti et al. |
| 2010/0294986 A1 | 11/2010 | Sultana et al. |
| 2010/0304355 A1 | 12/2010 | Shuler et al. |
| 2010/0323439 A1 | 12/2010 | Takayama et al. |
| 2011/0000482 A1 | 1/2011 | Gumaste et al. |
| 2011/0027804 A1 | 2/2011 | Yarmush et al. |
| 2011/0053207 A1 | 3/2011 | Hoganson et al. |
| 2011/0086382 A1 | 4/2011 | Marx |
| 2011/0183312 A1 | 7/2011 | Huang |
| 2011/0269226 A1 | 11/2011 | Van Noort et al. |
| 2011/0287469 A1 | 11/2011 | Guenther et al. |
| 2012/0003732 A1 | 1/2012 | Hung et al. |
| 2012/0088693 A1 | 4/2012 | Lee et al. |
| 2012/0135446 A1 | 5/2012 | Collins et al. |
| 2012/0135452 A1 | 5/2012 | Shuler et al. |
| 2012/0199487 A1 | 8/2012 | Stelzle et al. |
| 2012/0214189 A1 | 8/2012 | Shuler et al. |
| 2012/0318726 A1 | 12/2012 | Charest et al. |
| 2012/0322097 A1 | 12/2012 | Charest et al. |
| 2013/0059322 A1 | 3/2013 | Hung et al. |
| 2013/0109594 A1 | 5/2013 | Gonda et al. |

(56) References Cited

U.S. PATENT DOCUMENTS

FOREIGN PATENT DOCUMENTS

| | | |
|---|---|---|
| EA | 200601901 A1 | 4/2007 |
| EP | 0539383 B1 | 9/1996 |
| EP | 0637996 B1 | 7/1997 |
| EP | 0823483 A1 | 2/1998 |
| EP | 0637997 B1 | 7/1998 |
| EP | 1820846 A1 | 8/2007 |
| ES | 2287351 T3 | 12/2007 |
| FR | 1598245 | 7/1970 |
| FR | 2786783 A1 | 6/2000 |
| GB | 863707 | 3/1961 |
| JP | 4152885 B2 | 9/2008 |
| RU | 2168174 C2 | 5/2001 |
| RU | 2275913 C2 | 5/2006 |
| RU | 2301677 C1 | 6/2007 |
| WO | 82/03227 A1 | 9/1982 |
| WO | 91/02049 A1 | 2/1991 |
| WO | 93/11498 A1 | 6/1993 |
| WO | 99/47922 A2 | 9/1999 |
| WO | 03/082145 | 10/2003 |
| WO | 03/082145 A2 | 10/2003 |
| WO | 2004/101743 A2 | 11/2004 |
| WO | 2005100537 A1 | 10/2005 |
| WO | 2006/047758 A1 | 5/2006 |
| WO | 2007/021343 A2 | 2/2007 |
| WO | 2008/040015 A2 | 4/2008 |
| WO | 2008/051265 A2 | 5/2008 |
| WO | 2009/089189 A2 | 7/2009 |
| WO | 2010/009307 A2 | 1/2010 |
| WO | 2010/062911 A2 | 6/2010 |
| WO | 2010/123594 A2 | 10/2010 |
| WO | 2011/014674 A2 | 2/2011 |
| WO | 2012/016711 A1 | 2/2012 |
| WO | 2012/118799 A2 | 9/2012 |
| WO | 2012/154729 A1 | 11/2012 |
| WO | 2012/154834 A1 | 11/2012 |
| WO | 2013/056019 A1 | 4/2013 |

OTHER PUBLICATIONS

El-Ali et al., Nature, 442:403-411 (2006). "Cells on chips."
Fernandes et al., Trends in Biotechnology, 27(6):342-349 (2009). "High-throughput cellular microarray platforms: applications in drug discovery, toxicology and stem cell research."
Huh et al., Science, 328:1662-1668 (2010). "Reconstituting Organ-Level Lung Functions on a Chip."
Huh et al., Science Translational Medicine, 4(159):159ra147 (2012). "A Human Disease Model of Drug Toxicity-Induced Pulmonary Edema in a Lung-on-a-Chip Microdevice."
Kang et al., Drug Discovery Today, 13(1/2):1-13 (2008). "Microfluidics for drug discovery and development: From target selection to product lifecycle management."
Khademhosseini et al., PNAS, 103(8):2480-2487 (2006). "Microscale technologies for tissue engineering and biology."
Khetani et al., Nature Biotechnology, 26(1):120-126 (2008). "Microscale culture of human liver cells for drug development."
Kim et al., Lab Chip, DOI: 10.1039/c21c70074j (2012). "Human gut-on-a-chip inhabited by microbial flora that experiences intestinal perstalsis-like motions and flow."
Kola, Clinical Pharmacology & Therapeutics, 83(2):227-230 (2008). "The State of Innovation in Drug Development."
Maguire et al., Current Drug Metabolism, 10:1192-1199 (2009). "Design and Application of Microfluidic Systems for In Vitro Pharmacokinetic Evaluation of Drug Candidates."
Meyvantsson et al., Annu. Rev. Anal. Chem., 1:423-449 (2008). "Cell Culture Models in Microfluidic Systems."
Munos, Nature Reviews Drug Discovery, 8:959-968 (2009). "Lessons from 60 years of pharmaceutical innovation."
Sung et al., Lap Chip, 9:1385-1394 (2009). "A micro cell culture analogy (µCCA) with 3-D hydrogel culture of multiple cell lines to assess metabolism-dependent cytotoxicity of anti-cancer drugs."
Whitesides, Nature, 442(27):368-373 (2006). "The origins and the future of microfluidics."
Huh et al., PNAS, 104(48):18886-18891 (2007). "Acoustically detectable cellular-level lung injury induced by fluid mechanical stresses in microfluidic airway systems."
Lee et al., J Biomed Mater Res 90A:619-628 (2009). "Hydrophilic electrospun polyurethane nanofiber matrices for hMSC culture in a microfluidic cell chip."
Ong et al., Biomaterials, 29:3237-3244 (2008). "A gel-free 3D microfluidic cell culture system."
Shin et al., Biomedical Microdevices, 6(4):269-278 (2004). "Endothelialized Networks with a Vascular Geometry in Microfabricated Poly(dimethyl siloxane)."
Song et al., Anal. Chem., 77:3993-3999 (2005). "Computer-Controlled Microcirculatory Support System for Endothelial Cell Culture and Shearing."
Sung et al., Lab Chip, 9:1385-1394 (2009). "A micro cell culture analog (µCCA) with 3-D hydrogel culture of multiple cell lines to assess metabolism-dependent cytotoxicity of anti-cancer drugs."
Zhang et al., Lab Chip, 9:3185-3192 (2009). "Towards a human-on-chip: Culturing multiple cell types on a chip with compartmentalized microenvironments."
Sung et al., Biomed Microdevices, 11:731-738 (2009). "Prevention of air bubble formation in a microfluidic perfusion cell culture system using a microscale bubble trap."
Sweeney et al., Toxic. In Vitro, 9(3):307-316 (1995). "A Cell Culture Analogue of Rodent Physiology: Application to Naphthalene Toxicology."
Tatosian et al., Biotechnology and Bioengineering, 103(1):187-198 (2009). "A Novel System for Evaluation of Drug Mixtures for Potential Efficacy in Treating Multidrug Resistant Cancers".
Viravaidya et al., Biotechnol. Prog., 20:316-323 (2004). "Development of a Microscale Cell Culture Analog to Probe Napthalene Toxicity".
Viravaidya et al., Biotechnol. Prog., 20:590-597 (2004). "Incorporation of 3T3-L1 Cells to Mimic Bioaccumulation in a Microscale Cell Culture Analog Device for Toxicity Studies."
Warnke et al., Lancet, 364:766-770 (2004). "Growth and transplantation of a custom vascularised bone graft in a man."
Williamson et al., Methods in Cell Biology, 66:339-364 (2001). "Phosphatidylserine Exposure and Phagocytosis of Apoptotic Cells."
Wronski et al., BioTechniques, 32:666-668 (2002). "Two-Color, Fluorescence-Based Microplate Assay for Apoptosis Detection".
Yamazaki et al., Drug Metabolism and Disposition, 29(6):794-797 (2001). "Rat Cytochrome P450 1A and 3A Enzymes Involved in Bioactivation of Tegafur to 5-Fluorouracil and Autoinduced by Tegafur in Liver Microsomes".
Yao e al., American Journal of Pathology, 166(2):625-636 (2005). "Targeting Pancreatic Islets with Phage Display Assisted by Laser Pressure Catapult Microdissection".
Yung et al., Lab Chip, 9:1171-1177 (2009). "Micromagnetic-microfluidic blood cleansing device."
McAuliffe et al., Mol Cell Biomech, 5(2):119-132 (2008). "Development of a gastrointestinal tract microscale cell culture analog to predict drug transport".
Ball et al., Compu. Biol. Med., 24(4):269-276 (1994). "CMATRIX: Software for Physiologically Based Pharmacokinetic Modeling Using a Symbolic Matrix Representation System."
Baudoin et al., Toxicology in Vitro, 21:535-544 (2007). "Trends in the development of microfluidic cell biochips for in vitro hepatoxicity."
Buckpitt et al., The Journal of Pharmacology and Experimental Therapeutics, 231(2):291-300 (1984). "Hepatic and Pulmonary Microsomal Metabolism of Naphthalene to Glutathione Adducts: Factors Affecting the Relative Rates of Conjugate Formation."
Camp et al., Biomed Microdevices, 10:179-186 (2008). "Fabrication of a multiple-diameter branched network of microvascular channels with semi-circular cross-sections using xenon difluoride etching."
Chao et al., Biochemical Pharmacology, 78:625-632 (2009). "Evaluation of a microfluidic based cell culture platform with primary human hepatocytes for the prediction of hepatic clearance in human."
Cheng et al., Lab Chip, 7:763-769 (2007). "A hydrogel-based microfluidic device for the studies of directed cell migration."

(56) References Cited

OTHER PUBLICATIONS

Delraso, Toxicology Letters, 68:91-99 (1993). "In vitro methodologies for enhanced toxicity testing."
D'Souza et al, The Journal of Pharmacology and Experimental Therapeutics, 245(2):563-568 (1988). "Physiological Model for Tissue Glutathione Depletion and Increased Resynthesis after Ethylene Dichloride Exposure."
Frampton et al., J. Neural Eng., 4:399-409 (2007). "Three-dimensional hydrogel cultures for modeling changes in tissue impedance around microfabricated neural probes."
Frampton et al., Central Nervous System Agents in Medicinal Chemistry, 8:203-219 (2008). "Biomedical Technologies for In Vitro Screening and Controlled Delivery of Neuroactive Compounds."
Ghanem et al., Biotechnol. Prog., 16:334-345 (2000). "Combining Cell Culture Analogue Reactor Designs and PBPK Models to Probe Mechanisms of Naphthalene Toxicity."
Ghanem et al., Biotechnol. Prog., 16:471-479 (2000). "Characterization of a Perfusion Reactor Utilizing Mammalian Cells on Microcarrier Beads."
Haddad et al., Toxicology Letters, 85:113-126 (1996). "A methodology for solving physiologically based pharmacokinetic models without the use of simulation softwares."
Haies et al., Am Rev Respir Dis, 123:533-541 (1981). "Morphometric Study of Rat Lung Cells. I. Numerical and Dimensional Characteristics of Parenchymal Cell Population."
Harris et al., Biotechnology and Bioprocess Engineering, 8:246-251 (2003). "Growth of Endothelial Cells on Microfabricated Silicon Nitride Membranes for an In Vitro Model of the Blood-brain Barrier."
Harris et al., Bioengineering Conference, Apr. 20-21, 2002. Proceedings of the IEEE 28th Annual Northeast. "Development of a Physiologically Based In Vitro Model of the Blood-Brain Barrier."
Heuschkel et al., Sensors and Actuators B, 48:356-361 (1998). "Buried microchannels in photopolymer for delivering of solutions to neurons in a network."
Hoang, Toxicology Letters, 79:99-106 (1995). "Physiologically based pharmacokinetic models: mathematical fundamentals and simulation implementations."
Hodgson, Nature Biotechnology, 19:722-726 (2001). "ADMET-turning chemicals into drugs."
Hwang, Nature Medicine, 7(10):1111-1117 (2001). "Ferredoxin reductase affects p53-dependent, 5-fluorouracil-induced apoptosis in colorectal cancer cells."
Ikeda et al., Clinical Cancer Research, 6:4409-4415 (2000). "Bioactivation of Tegafur to 5-Fluorouracil Is Catalyzed by Cytochrome P-450 2A6 in Human Liver Microsomes in Vitro."
Jones et al., TIBTECH, 17:477-481 (1999). "Glowing jellyfish, luminescence and a molecule called coelenterazine."
Kim et al., Optical Diagnostics and Sensing IV, Proceedings of SPIE, 5325:122-127 (2004). "Investigation of doxorubicin for multi-drug resistance using a fluorescent cytometric imaging system integrated onto cell culture analog devices."
Kim et al., Sensors and Actuators B, 128:108-116 (2007). "Microfluidic biomechanical device for compressive cell stimulation and lysis."
Knaak et al., Toxicology Letters, 79:87-98 (1995). "Development of partition coefficients, Vmax and Km values, and allometric relationships."
Koebe et al., Toxicology, 154:31-44 (2000). "In vitro toxicology in hepatocyte bioreactors-extracellular acidification rate (EAR) in a target cell line indicates hepato-activated transformation of substrates."
Komatsu et al., Drug Metabolism and Disposition, 28(12):1457-1463 (2000). "Roles of Cytochromes P450 1A6, and 2C8 in 5-Fluorouracil Formation from Tegafur, an Anticancer Prodrug, in Human Liver Microsomes."
Lehmann et al., Animal Cell Biotechnology, 3:221-237 (1988). "8. Bubble-free Reactors and Their Development for Continuous Culture with Cell Recycle."
Li et al., Cytometry, 20:172-180 (1995). "Single-Step Procedure for Labeling DNA Strand Breaks With Fluorescein- or BODIPY-Conjugated Deoxynucleotides: Detection of Apoptosis and Bromodeoxyuridine Incorporation."
Ma et al., Lab Chip, 5:74-85 (2005). "An endothelial and astrocyte co-culture model fo the blood-brain barrier utilizing an ultra-thin, nanofabricated silicon nitride membrane."
Ma et al., Lab Chip, 9:232-238 (2009). "Characterization of drug metabolites and cytotoxicity assay simultaneously using an integrated microfluidic device."
Maguire et al., Current Drug Metabolism, 10:000-000 (2009). "Design and Application of Microfluidic Systems for In Vitro Pharmacokinetic Evaluation of Drug Candidates."
Mahler et al., Biotechnology and Bioengineering, 104(1):193-205 (2009). "Characterization of a Gastrointestinal Tract Microscale Cell Culture Analog Used to Predict Drug Toxicity."
Matsuda et al., ASAIO Journal, 40:M594-M597 (1994). "Microfabricated Surface Designs for Cell Culture and Diagnosis."
Oh et al., Cytometry Part A, 71A:857-865 (2007). "Real-Time Fluorescence Detection of Multiple Microscale Cell Culture Analog Devices In Situ."
Park et al., Biotechnol. Prog., 19:243-253 (2003). "Integration of Cell Culture and Microfabrication Technology."
Poulin et al., Journal of Pharmaceutical Sciences, 89(1):16-35 (2000). "A Priori Prediction of Tissue: Plasma Partition Coefficients of Drugs to Facilitate the Use of Physiologically-Based Pharmacokinetic Models in Drug Discovery."
Powers et al., Biotechnol Bioeng, 78:257-269 (2002). "A Microfabricated Array Bioreactor for Perfused 3D Liver Culture."
Powers et al., Tissue Engineering, 8(3):499-513 (2002). "Functional Behavior of Primary Rat Liver Cells in a Three-Dimensional Dimensional Perfused Microarray Bioreactor."
Qi et al., Lab Chip, 9:2184-2193 (2009). "Miniature inhalation therapy platform using surface acoustic wave microfluidic atomization."
Riley et al., Br. J. clin. Pharmac., 30:417-426 (1990). "Bioactivation of dapsone to a cytotoxic metabolite: in vitro use of a novel two compartment system which contains human tissues."
Rodriguez-Antona et al., Archives of Biochemistry and Biophysics, 376(1):109-116 (2000). "Quantitative RT-PCR Measurement of Human Cytochrome P-450s: Application to Drug Induction Studies."
Segelken, Cornell Chronicle, Sep. 21, 1999. "Impact of biotechnology will be examined Oct. 11 at Cornell symposium."
Sheridan et al., Burns, 27:421-424 (2001). "Initial experience with a composite autologous skin substitute."
Shuler et al., Biotechnology and Bioengineering, 52:45-60 (1996). "A Self-Regulating Cell Culture Analog Device to Mimic Animal and Human Toxicological Responses."
Sin et al., Proceedings of SPIE, 4560:98-101 (2001). "Animal on a chip: A Microscale Cell Culture Analog Device for evaluating Toxicological and Pharmacological."
Sin et al., Biotechnol. Prog., 20:338-345 (2004). "The Design and Fabrication of Three-Chamber Microscale Cell Culture Analog Devices with Integrated Dissolved Oxygen Sensors."
Sin et al., Biotechnol Bioeng., 85(3):359-363 (2004). "A Self-Priming Microfluidic Diaphragm Pump Capable of Recirculation Fabricated by Combining Soft Lithography and Traditional Machining."
Slob et al., Critical Reviews in Toxicology, 27(2):261-272 (1997). "Structural Identifiability of PBPK Models: Practical Consequences for Modeling Strategies and Study Designs."
Smyth et al., BioTechniques, 32:648-665 (2002). "Markers of Apoptosis: Methods for Elucidating the Mechanism of Apoptotic Cell Death from the Nervous System."
US 6,465,252, 10/2002, Toner et al. (withdrawn)

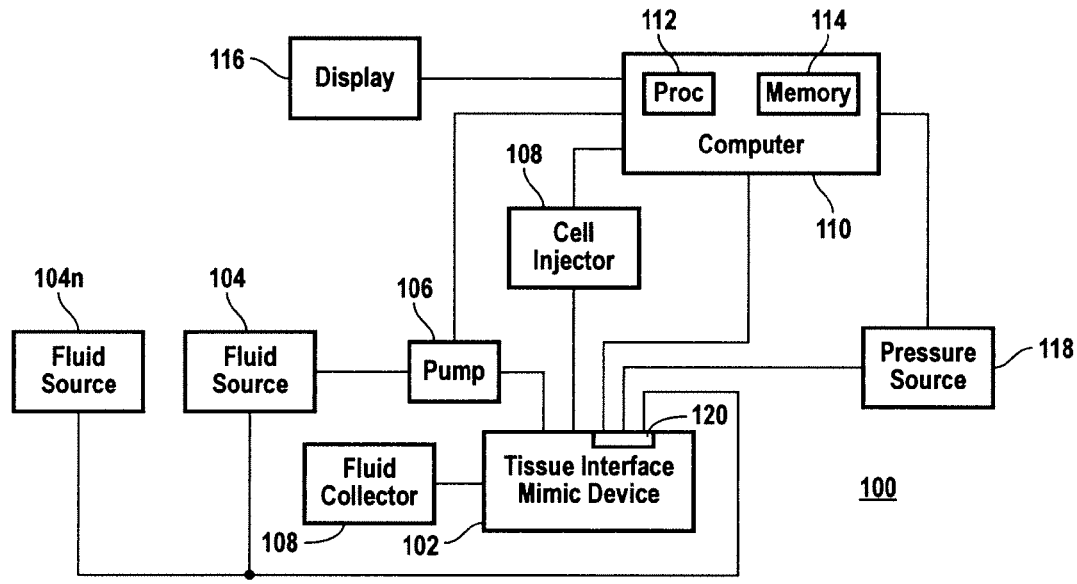
FIG. 1
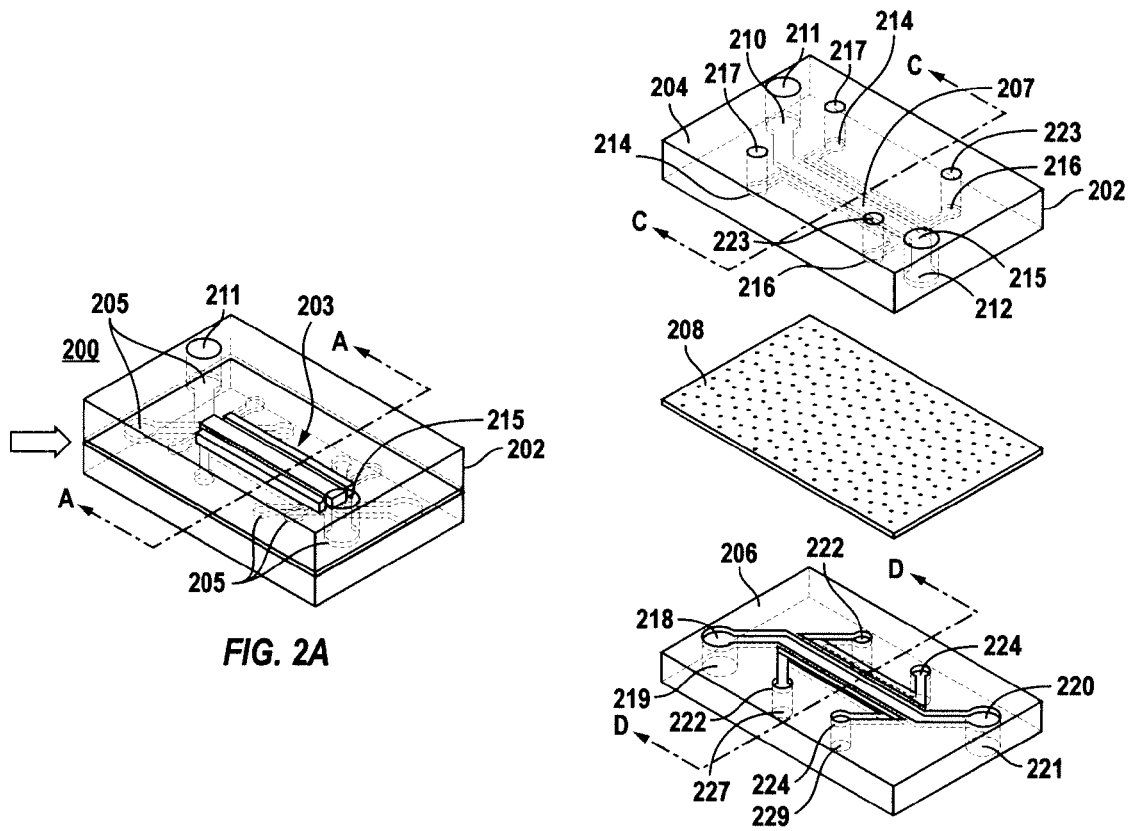
FIG. 2A
FIG. 2B

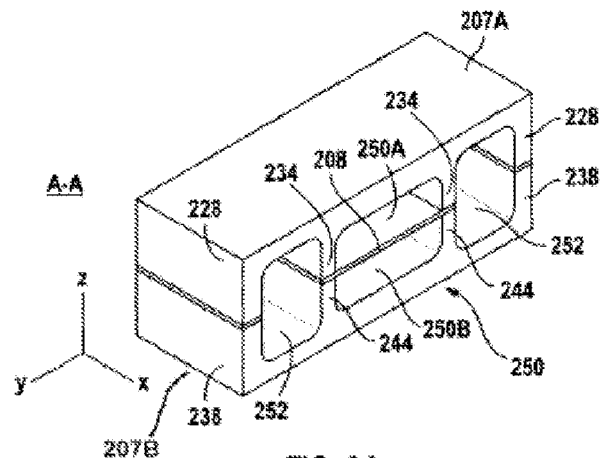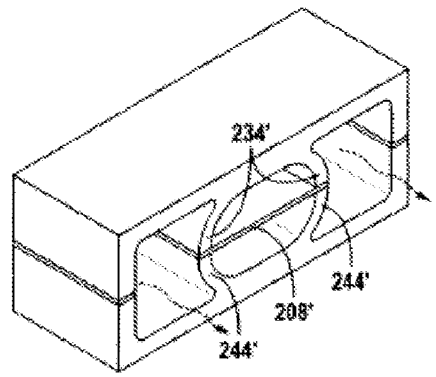
FIG. 3A  FIG. 3B
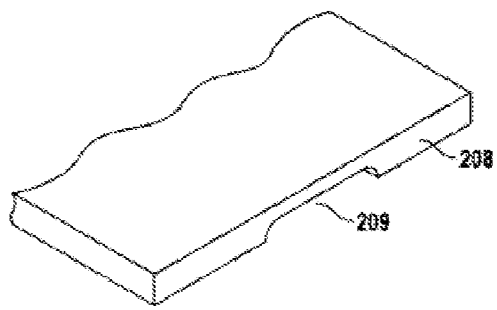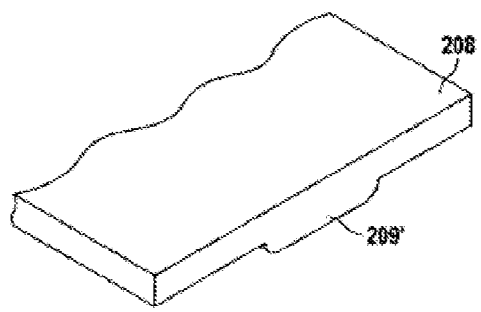
FIG. 3C  FIG. 3D
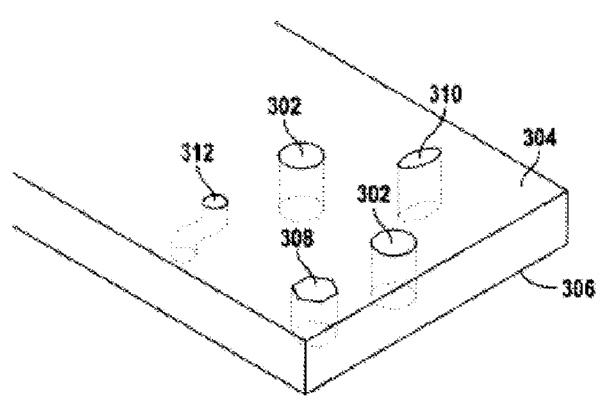
FIG. 3E

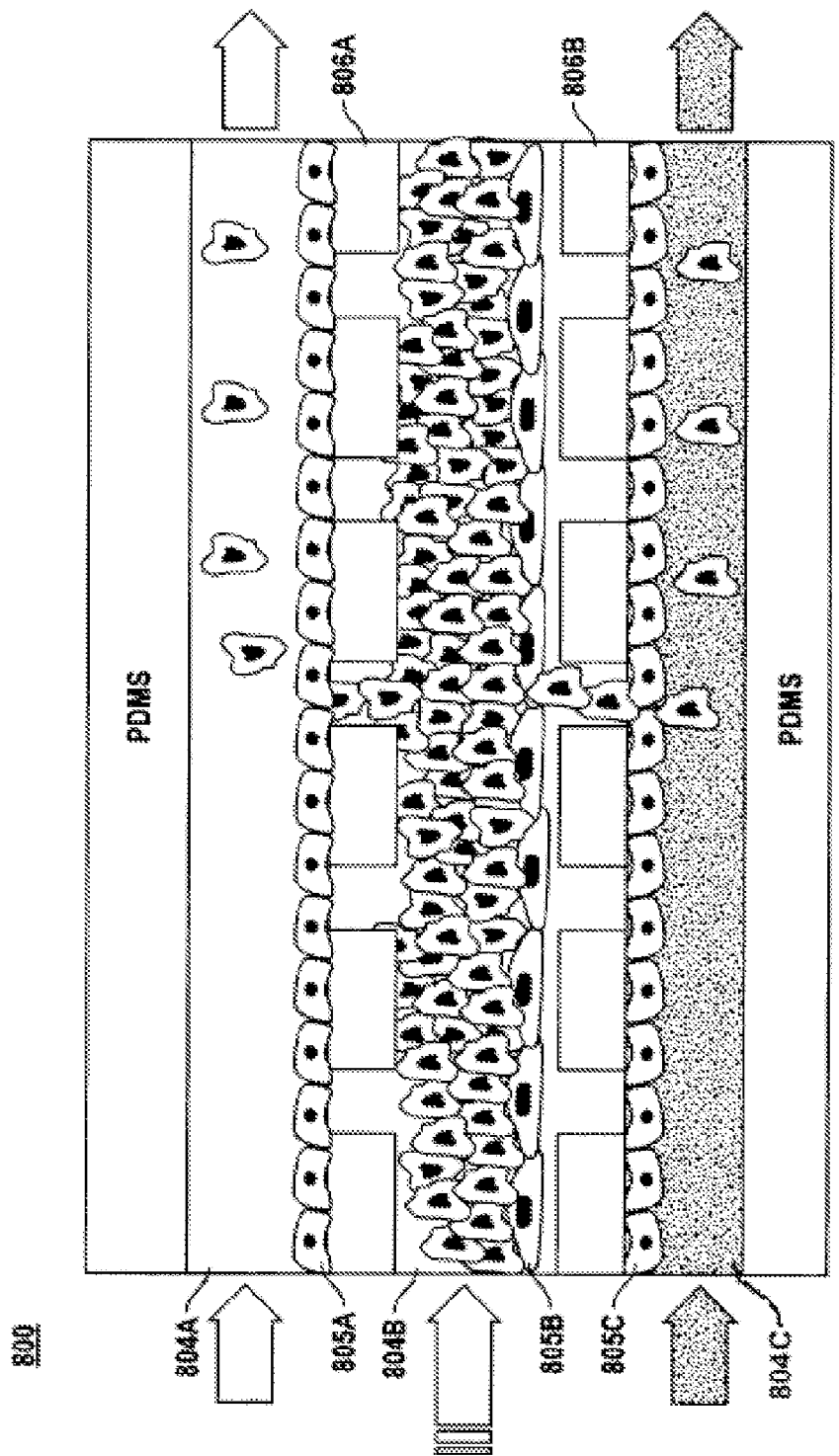

ORGAN MIMIC DEVICE WITH MICROCHANNELS AND METHODS OF USE AND MANUFACTURING THEREOF

GOVERNMENT SUPPORT

This invention was made with Government support under Grant No. NIH R01 ES016665-01A1 awarded by the National Institutes of Health. The Government has certain rights in the invention.

CROSS REFERENCE TO RELATED APPLICATIONS

This application is a 371 National Phase Entry Application of International Application No. PCT/US2009/050830 filed Jul. 16, 2009, which designates the U.S., and which claims the benefit of priority under 35 U.S.C. §119(e) of U.S. Provisional Application No. 61/081,080 filed Jul. 16, 2008, the contents of which are incorporated herein by reference in their entirety.

TECHNICAL FIELD

The present disclosure relates generally to an organ mimic device with microchannels and methods of use and manufacturing thereof.

BACKGROUND

Mechanical forces—pushes, pulls, tensions, compressions—are important regulators of cell development and behavior. Tensegrity provides the structure that determines how these physical forces are distributed inside a cell or tissue, and how and where they exert their influence.

In the human body, most cells are constantly subjected to mechanical forces, such as tension or compression. Application of mechanical strain to cells in culture simulates the in vivo environment, causing dramatic morphologic changes and biomechanical responses in the cells. There are both long and short term changes that occur when cells are mechanically loaded in culture, such as alterations in the rate and amount of DNA or RNA synthesis or degradation, protein expression and secretion, the rate of cell division and alignment, changes in energy metabolism, changes in rates of macromolecular synthesis or degradation, and other changes in biochemistry and bioenergetics.

Every cell has an internal scaffolding, or cytoskeleton, a lattice formed from molecular "struts and wires". The "wires" are a crisscrossing network of fine cables, known as microfilaments, that stretch from the cell membrane to the nucleus, exerting an inward pull. Opposing the pull are microtubules, the thicker compression-bearing "struts" of the cytoskeleton, and specialized receptor molecules on the cell's outer membrane that anchor the cell to the extracellular matrix, the fibrous substance that holds groups of cells together. This balance of forces is the hallmark of tensegrity.

Tissues are built from groups of cells, like eggs sitting on the "egg carton" of the extracellular matrix. The receptor molecules anchoring cells to the matrix, known as integrins, connect the cells to the wider world. Mechanical force on a tissue is felt first by integrins at these anchoring points, and then is carried by the cytoskeleton to regions deep inside each cell. Inside the cell, the force might vibrate or change the shape of a protein molecule, triggering a biochemical reaction, or tug on a chromosome in the nucleus, activating a gene.

Cells also can be said to have "tone," just like muscles, because of the constant pull of the cytoskeletal filaments. Much like a stretched violin string produces different sounds when force is applied at different points along its length, the cell processes chemical signals differently depending on how much it is distorted.

A growth factor will have different effects depending on how much the cell is stretched. Cells that are stretched and flattened, like those in the surfaces of wounds, tend to grow and multiply, whereas rounded cells, cramped by overly crowded conditions, switch on a "suicide" program and die. In contrast, cells that are neither stretched nor retracted carry on with their intended functions.

Another tenet of cellular tensegrity is that physical location matters. When regulatory molecules float around loose inside the cell, their activities are little affected by mechanical forces that act on the cell as a whole. But when they're attached to the cytoskeleton, they become part of the larger network, and are in a position to influence cellular decision-making. Many regulatory and signaling molecules are anchored on the cytoskeleton at the cell's surface membrane, in spots known as adhesion sites, where integrins cluster. These prime locations are key signal-processing centers, like nodes on a computer network, where neighboring molecules can receive mechanical information from the outside world and exchange signals.

Thus, assessing the full effects of drugs, drug delivery vehicles, nanodiagnostics or therapies or environmental stressors, such as particles, gases, and toxins, in a physiological environment requires not only a study of the cell-cell and cell-chemical interactions, but also a study of how these interactions are affected by physiological mechanical forces in both healthy tissues and tissues affected with diseases.

Methods of altering the mechanical environment or response of cells in culture have included wounding cells by scraping a monolayer, applying magnetic or electric fields, or by applying static or cyclic tension or compression with a screw device, hydraulic pressure, or weights directly to the cultured cells. Shear stress has also been induced by subjecting the cells to fluid flow. However, few of these procedures have allowed for quantitation of the applied strains or provided regulation to achieve a broad reproducible range of cyclic deformations within a culture microenvironment that maintains physiologically relevant tissue-tissue interactions.

Living organs are three-dimensional vascularized structures composed of two or more closely apposed tissues that function collectively and transport materials, cells and information across tissue-tissue interfaces in the presence of dynamic mechanical forces, such as fluid shear and mechanical strain. Creation of microdevices containing living cells that recreate these physiological tissue-tissue interfaces and permit fluid flow and dynamic mechanical distortion would have great value for study of complex organ functions, e.g., immune cell trafficking, nutrient absorption, infection, oxygen and carbon dioxide exchange, etc., and for drug screening, toxicology, diagnostics and therapeutics.

The alveolar-capillary unit plays a vital role in the maintenance of normal physiological function of the lung as well as in the pathogenesis and progression of various pulmonary diseases. Because of the complex architecture of the lung, the small size of lung alveoli and their surrounding microvessels, and the dynamic mechanical motions of this organ, it is difficult to study this structure at the microscale.

The lung has an anatomically unique structure having a hierarchical branching network of conducting tubes that enable convective gas transport to and from the microscopic alveolar compartments where gas exchange occurs. The alveolus is the most important functional unit of the lung for normal respiration, and it is most clinically relevant in that it is the blood-gas barrier or interface, as well as the site where surfactants act to permit air entry and where immune cells, pathogens and fluids accumulate in patients with acute respiratory distress syndrome (ARDS) or infections, such as pneumonia.

The blood-gas barrier or tissue-tissue interface between the pulmonary capillaries and the alveolar lumen is composed of a single layer of alveolar epithelium closely juxtaposed to a single layer of capillary endothelium separated by a thin extracellular matrix (ECM), which forms through cellular and molecular self-assembly in the embryo. Virtually all analysis of the function of the alveolar-capillary unit has been carried out in whole animal studies because it has not been possible to regenerate this organ-level structure in vitro.

A major challenge lies in the lack of experimental tools that can promote assembly of multi-cellular and multi-tissue organ-like structures that exhibit the key structural organization, physiological functions, and physiological or pathological mechanical activity of the lung alveolar-capillary unit, which normally undergoes repeated expansion and contraction during each respiratory cycle. This limitation could be overcome if it were possible to regenerate this organ-level structure and recreate its physiological mechanical microenvironment in vitro. However, this has not been fully accomplished.

What is needed is a organ mimic device capable of being used in vitro or in vivo which performs tissue-tissue related functions and which also allows cells to naturally organize in the device in response to not only chemical but also mechanical forces and allows the study of cell behavior through a membrane which mimics tissue-tissue physiology.

OVERVIEW

System and method comprises a body having a central microchannel separated by one or more porous membranes. The membranes are configured to divide the central microchannel into a two or more closely apposed parallel central microchannels, wherein one or more first fluids are applied through the first central microchannel and one or more second fluids are applied through the second or more central microchannels. The surfaces of each porous membrane can be coated with cell adhesive molecules to support the attachment of cells and promote their organization into tissues on the upper and lower surface of each membrane, thereby creating one or more tissue-tissue interfaces separated by porous membranes between the adjacent parallel fluid channels. The membrane may be porous, flexible, elastic, or a combination thereof with pores large enough to only permit exchange of gases and small chemicals, or large enough to permit migration and transchannel passage of large proteins, as well as whole living cells. Fluid pressure, flow characteristics and channel geometry also may be varied to apply a desired fluid shear stress to one or both tissue layers.

In an embodiment, operating channels adjacent to the central channel are applied a positive or negative pressure which creates a pressure differential that causes the membrane to selectively expand and retract in response to the pressure, thereby further physiologically simulating mechanical force of a living tissue-tissue interface.

In another embodiment, three or more parallel microchannels are separated by a plurality of parallel porous membranes which are lined by a common tissue type in the central channel and two different tissue types on the opposite sides of the membranes in the two outer channels. An example would be a cancer mimic device in which cancer cells are grown in the central microchannel and on the inner surfaces of both porous membranes, while capillary endothelium is grown on the opposite surface of one porous membrane and lymphatic endothelium is grown on the opposite surface of the second porous membrane. This recreates the tumor microarchitecture and permits study of delivery of oxygen, nutrients, drugs and immune cells via the vascular conduit as well as tumor cell egress and metastasis via the lymphatic microchannel.

BRIEF DESCRIPTION OF THE DRAWINGS

The accompanying drawings, which are incorporated into and constitute a part of this specification, illustrate one or more examples of embodiments and, together with the description of example embodiments, serve to explain the principles and implementations of the embodiments. In the drawings:

FIG. 1 illustrates a block diagram of a system employing an example organ mimic device in accordance with an embodiment.

FIG. 2A illustrates a perspective view of a organ mimic device in accordance with an embodiment.

FIG. 2B illustrates an exploded view of the organ mimic device in accordance with an embodiment.

FIGS. 3A-3B illustrate perspective views of tissue-tissue interface regions of the device in accordance with an embodiment.

FIGS. 3C-3E illustrate perspective views of the membrane in accordance with one or more embodiments.

FIG. 7C illustrates a side view of the membrane of the organ mimic device in accordance with an embodiment.

DESCRIPTION OF EXAMPLE EMBODIMENTS

Figure 2C:
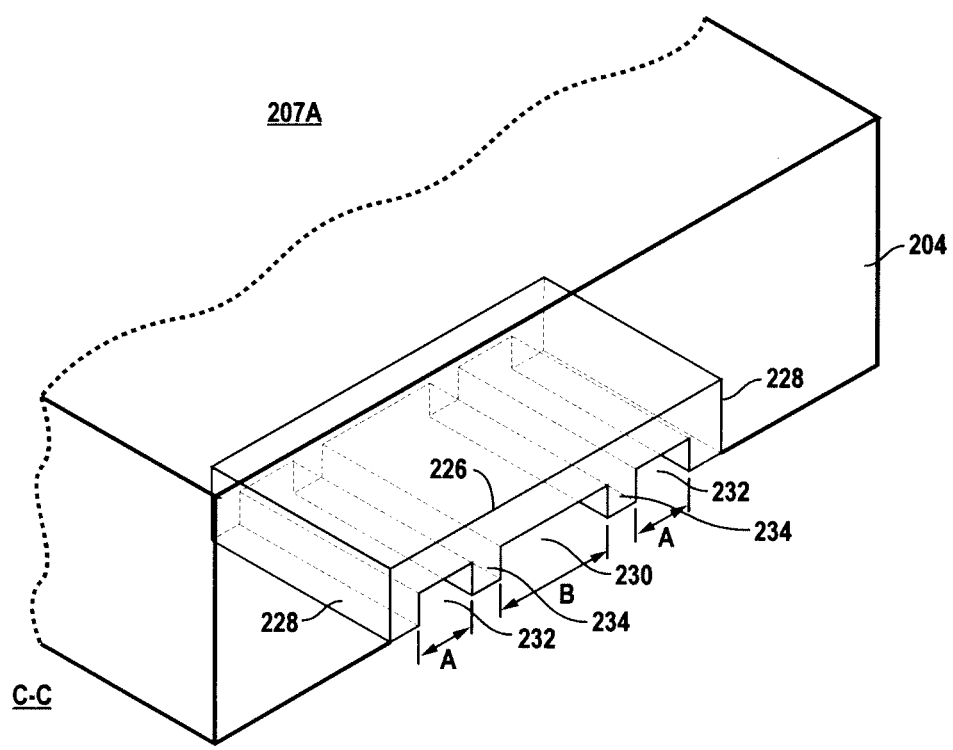
FIGS. 2C-2D illustrate perspective views of tissue-tissue interface regions of the device in accordance with an embodiment.

Example embodiments are described herein in the context of an organ simulating device and methods of use and manufacturing thereof. Those of ordinary skill in the art will realize that the following description is illustrative only and is not intended to be in any way limiting. Other embodiments will readily suggest themselves to such skilled persons having the benefit of this disclosure. Reference will now be made in detail to implementations of the example embodiments as illustrated in the accompanying drawings. The same reference indicators will be used throughout the drawings and the following description to refer to the same or like items. It is understood that the phrase "an embodiment" encompasses more than one embodiment and is thus not limited to only one embodiment for brevity's sake.

In accordance with this disclosure, the organ mimic device (also referred to as "present device") is preferably utilized in an overall system incorporating sensors, computers, displays and other computing equipment utilizing software, data components, process steps and/or data structures. The components, process steps, and/or data structures described herein with respect to the computer system with which the organ mimic device is employed may be implemented using various types of operating systems, computing platforms, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used without departing from the scope and spirit of the inventive concepts disclosed herein.

Where a method comprising a series of process steps is implemented by a computer or a machine with use with the organ mimic device described below and those process steps can be stored as a series of instructions readable by the machine, they may be stored on a tangible medium such as a computer memory device (e.g., ROM (Read Only Memory), PROM (Programmable Read Only Memory), EEPROM (Electrically Eraseable Programmable Read Only Memory), FLASH Memory, Jump Drive, and the like), magnetic storage medium (e.g., tape, magnetic disk drive, and the like), optical storage medium (e.g., CD-ROM, DVD-ROM, paper card, paper tape and the like) and other types of program memory.

Embodiments of the present device can be applied in numerous fields including basic biological science, life science research, drug discovery and development, drug safety testing, chemical and biological assays, as well as tissue and organ engineering. In an embodiment, the organ mimic device can be used as microvascular network structures for basic research in cardiovascular, cancer, and organ-specific disease biology. Furthermore, one or more embodiments of the device find application in organ assist devices for liver, kidney, lung, intestine, bone marrow, and other organs and tissues, as well as in organ replacement structures.

The cellular responses to the various environmental cues can be monitored using various systems that can be combined with the present device. One can monitor changes in pH using well known sensors. One can also sample cells, continuously or periodically for measurement of changes in gene transcription or changes in cellular biochemistry or structural organization. For example, one can measure reactive oxygen species (ROIs) that are a sign of cellular stress. One can also subject the "tissue" grown on the porous membrane to microscopic analysis, immunohistochemical analysis, in situ hybridization analysis, or typical pathological analysis using staining, such as hematoxylin and eosin staining. Samples for these analysis can be carried out in real-time, or taken after an experiment or by taking small biopsies at different stages during a study or an experiment.

One can subject the cells grown on the membrane to other cells, such as immune system cells or bacterial cells, to antibodies or antibody-directed cells, for example to target specific cellular receptors. One can expose the cells to viruses or other particles. To assist in detection of movement of externally supplied substances, such as cells, viruses, particles or proteins, one can naturally label them using typical means such as radioactive or fluorescent labels.

Cells can be grown, cultured and analyzed using the present device for 1, 2, 3, 4, 5, 6, or 7 days, between at least 1-2 weeks, and even over 2 weeks. For example, as discussed below, it has been shown that co-culture of alveolar epithelial cells with pulmonary microvascular endothelial cells on a thin porous membrane in an embodiment of the described device could be grown for over two weeks without loss of viability of the cells.

The organ mimic device described herein has many different applications including, but not limited to, identification of markers of disease; assessing efficacy of anti-cancer therapeutics; testing gene therapy vectors; drug development; screening; studies of cells, especially stem cells and bone marrow cells; studies on biotransformation, absorption, clearance, metabolism, and activation of xenobiotics; studies on bioavailability and transport of chemical or biological agents across epithelial or endothelial layers; studies on transport of biological or chemical agents across the blood-brain barrier; studies on transport of biological or chemical agents across the intestinal epithelial barrier; studies on acute basal toxicity of chemical agents; studies on acute local or acute organ-specific toxicity of chemical agents; studies on chronic basal toxicity of chemical agents; studies on chronic local or chronic organ-specific toxicity of chemical agents; studies on teratogenicity of chemical agents; studies on genotoxicity, carcinogenicity, and mutagenicity of chemical agents; detection of infectious biological agents and biological weapons; detection of harmful chemical agents and chemical weapons; studies on infectious diseases; studies on the efficacy of chemical or biological agents to treat disease; studies on the optimal dose range of agents to treat disease; prediction of the response of organs in vivo to biological agents; prediction of the pharmacokinetics of chemical or biological agents; prediction of the pharmacodynamics of chemical or biological agents; studies concerning the impact of genetic content on response to agents; studies on gene transcription in response to chemical or biological agents; studies on protein expression in response to chemical or biological agents; studies on changes in metabolism in response to chemical or biological agents. The organ mimic device can also be used to screen on the cells, for an effect of the cells on the materials (for example, in a manner equivalent to tissue metabolism of a drug).

The present device may be used by one to simulate the mechanical load environment of walking, running, breathing, peristalsis, flow of flow or urine, or the beat of a heart, to cells cultured from mechanically active tissues, such as heart, lung, skeletal muscle, bone, ligament, tendon, cartilage, smooth muscle cells, intestine, kidney, endothelial cells and cells from other tissues. Rather than test the biological or biochemical responses of a cell in a static environment, the investigator can apply a range of frequencies, amplitudes and duration of mechanical stresses, including tension, compression and shear, to cultured cells.

A skilled artisan can implant various types of cells on the surfaces of the membrane. Cells include any cell type from a multicellular structure, including nematodes, amoebas, up to mammals such as humans. Cell types implanted on the device depend on the type of organ or organ function one wishes to mimic, and the tissues that comprise those organs. More details of the various types of cells implantable on the membrane of the present device are discussed below.

One can also co-culture various stem cells, such as bone marrow cells, induced adult stem cells, embryonal stem cells or stem cells isolated from adult tissues on either or both sides of the porous membrane. Using different culture media in the chambers feeding each layer of cells, one can allow different differentiation cues to reach the stem cell layers thereby differentiating the cells to different cell types. One can also mix cell types on the same side of the membrane to create co-cultures of different cells without membrane separation.

Using the organ mimic device described herein, one can study biotransformation, absorption, clearance, metabolism, and activation of xenobiotics, as well as drug delivery. The bioavailability and transport of chemical and biological agents across epithelial layers as in the intestine, endothelial layers as in blood vessels, and across the blood-brain barrier can also be studied. The acute basal toxicity, acute local toxicity or acute organ-specific toxicity, teratogenicity, genotoxicity, carcinogenicity, and mutagenicity, of chemical agents can also be studied. Effects of infectious biological agents, biological weapons, harmful chemical agents and chemical weapons can also be detected and studied. Infectious diseases and the efficacy of chemical and biological agents to treat these diseases, as well as optimal dosage ranges for these agents, can be studied. The response of organs in vivo to chemical and biological agents, and the pharmacokinetics and pharmacodynamics of these agents can be detected and studied using the present device. The impact of genetic content on response to the agents can be studied. The amount of protein and gene expression in response to chemical or biological agents can be determined. Changes in metabolism in response to chemical or biological agents can be studied as well using the present device.

The advantages of the organ mimic device, as opposed to conventional cell cultures or tissue cultures, are numerous. For instance, when cells are placed in the organ mimic device, fibroblast, SMC (smooth muscle cell) and EC (endothelial cell) differentiation can occur that reestablishes a defined three-dimensional architectural tissue-tissue relationships that are close to the in vivo situation, and cell functions and responses to pharmacological agents or active substances or products can be investigated at the tissue and organ levels.

In addition, many cellular or tissue activities are amenable to detection in the organ mimic device, including, but not limited to, diffusion rate of the drugs into and through the layered tissues in transported flow channel; cell morphology, differentiation and secretion changes at different layers; cell locomotion, growth, apoptosis, and the like. Further, the effect of various drugs on different types of cells located at different layers of the system may be assessed easily.

For drug discovery, for example, there can be two advantages for using the organ mimic device described herein: (1) the organ mimic device is better able to mimic in vivo layered architecture of tissues and therefore allow one to study drug effect at the organ level in addition to at the cellular and tissue levels; and (2) the organ mimic device decreases the use of in vivo tissue models and the use of animals for drug selection and toxicology studies.

In addition to drug discovery and development, the organ mimic device described herein may be also useful in basic and clinical research. For example, the organ mimic device can be used to research the mechanism of tumorigenesis. It is well established that in vivo cancer progression is modulated by the host and the tumor micro-environment, including the stromal cells and extracellular matrix (ECM). For example, stromal cells were found being able to convert benign epithelial cells to malignant cells, thereby ECM was found to affect the tumor formation. There is growing evidence that cells growing in defined architecture are more resistant to cytotoxic agents than cells in mono layers. Therefore, a organ mimic device is a better means for simulating the original growth characteristics of cancer cells and thereby better reflects the real drug's sensitivity of in vivo tumors.

The organ mimic device can be employed in engineering a variety of tissues including, but not limited to, the cardiovascular system, lung, intestine, kidney, brain, bone marrow, bones, teeth, and skin. If the device is fabricated with a suitable biocompatible and/or biodegradable material, such as poly-lactide-co-glycolide acid (PLGA), the organ mimic device may be used for transplantation or implantation in vivo. Moreover, the ability to spatially localize and control interactions of several cell types presents an opportunity to engineer hierarchically, and to create more physiologically correct tissue and organ analogs. The arrangement of multiple cell types in defined arrangement has beneficial effects on cell differentiation, maintenance, and functional longevity.

The organ mimic device can also allow different growth factors, chemicals, gases and nutrients to be added to different cell types according to the needs of cells and their existence in vivo. Controlling the location of those factors or proteins may direct the process of specific cell remodeling and functioning, and also may provide the molecular cues to the whole system, resulting in such beneficial developments as neotissue, cell remodeling, enhanced secretion, and the like.

In yet another aspect, the organ mimic device can be utilized as multi cell type cellular microarrays, such as microfluidic devices. Using the organ mimic device, pattern integrity of cellular arrays can be maintained. These cellular microarrays may constitute the future "lab-on-a-chip", particularly when multiplexed and automated. These miniaturized multi cell type cultures will facilitate the observation of cell dynamics with faster, less noisy assays, having built-in complexity that will allow cells to exhibit in vivo-like responses to the array.

In yet another aspect, the organ mimic device can be utilized as biological sensors. Cell-based biosensors can provide more information than other biosensors because cells often have multifaceted physiological responses to stimuli, as well as novel mechanisms to amplify these responses. All cell types in the organ mimic device can be used to monitor different aspects of an analyte at the same time; different cell type in the organ mimic device can be used to monitor different analytes at the same time; or a mixture of both types of monitoring. Cells ranging from *E. coli* to cells of mammalian lines have been used as sensors for applications in environmental monitoring, toxin detection, and physiological monitoring.

In yet another aspect, the organ mimic device can be used in understanding fundamental processes in cell biology and cell-ECM interactions. The in vivo remodeling process is a complicated, dynamic, reciprocal process between cells and ECMs. The organ mimic device would be able to capture the complexity of these biological systems, rendering these systems amenable to investigation and beneficial manipulation. Furthermore, coupled with imaging tools, such as fluorescence microscopy, microfluorimetry or optical coherence tomography (OCT), real-time analysis of cellular behavior in the multilayered tissues is expected using the device. Examples of cell and tissue studies amenable to real-time analysis include cell secretion and signaling, cell-cell interactions, tissue-tissue interactions, dynamic engineered tissue construction and monitoring, structure-function investigations in tissue engineering, and the process of cell remodeling matrices in vitro.

Another example of the use of this device is to induce tissue-tissue interfaces and complex organ structures to form within the device by implanting it in vivo within the body of a living animal, and allowing cells and tissues to impregnate the device and establish normal tissue-tissue interfaces. Then the whole device and contained cells and tissues is surgically removed while perfusing it through one or more of the fluid channels with medium and gases necessary for cell survival. This complex organ mimic may then be maintained viable in vitro through continuous perfusion and used to study highly complex cell and tissue functions in their normal 3D context with a level of complexity not possible using any existing in vitro model system.

In particular, a microchannel device may be implanted subcutaneously in vivo into an animal in which the device contains bone-inducing materials, such as demineralized bone powder or bone morphogenic proteins (BMPs), in a channel that has one or more corresponding ports open to the surrounding tissue space. The second channel would be closed during implantation by closing its end ports or filling it with a solid removable materials, such as a solid rod. As a result of wound healing, connective tissues containing microcapillaries and mesenchymal stem cells would grow into the open channels of the device and, due to the presence of the bone-inducing material, will form bone with spaces that recruit circulating hematopoietic precursor cells to form fully functional bone marrow, as shown in past studies.

Once this process is complete, the surgical site would be reopened, and the second channel would be reopened by removing the rod or plugs and would then be connected with catheters linked to a fluid reservoir so that culture medium containing nutrients and gases necessary for cell survival could be pumped through the second channel and passed through the pores of the membrane into the first channel containing the formed bone marrow. The entire microchannel device could then be cut free from the surrounding tissue, and with the medium flowing continuously into the device, would be removed from the animal and passed to a tissue culture incubator and maintained in culture with continuous fluid flow through the second channel, and additional flow can be added to the first channel as well if desired by connecting to their inlet and outlet ports. The microchannel device would then be used to study intact bone marrow function in vitro as in a controlled environment.

Both biocompatible and biodegradable materials can be used in the present device to facilitate in vivo implantation of the present device. One can also use biocompatible and biodegradable coatings. For example, one can use ceramic coatings on a metallic substrate. But any type of coating material and the coating can be made of different types of materials: metals, ceramics, polymers, hydrogels or a combination of any of these materials.

Biocompatible materials include, but are not limited to an oxide, a phosphate, a carbonate, a nitride or a carbonitride. Among the oxide the following ones are preferred: tantalum oxide, aluminum oxide, iridium oxide, zirconium oxide or titanium oxide. In some cases the coating can also be made of a biodegradable material that will dissolve over time and may be replaced by the living tissue. Substrates are made of materials such as metals, ceramics, polymers or a combination of any of these. Metals such as stainless steel, Nitinol, titanium, titanium alloys, or aluminum and ceramics such as zirconia, alumina, or calcium phosphate are of particular interest.

The biocompatible material can also be biodegradable in that it will dissolve over time and may be replaced by the living tissue. Such biodegradable materials include, but are not limited to, poly(lactic acid-co-glycolic acid), polylactic acid, polyglycolic acid (PGA), collagen or other ECM molecules, other connective tissue proteins, magnesium alloys, polycaprolactone, hyaluric acid, adhesive proteins, biodegradable polymers, synthetic, biocompatible and biodegradable material, such as biopolymers, bioglasses, bioceramics, calcium sulfate, calcium phosphate such as, for example, monocalcium phosphate monohydrate, monocalcium phosphate anhydrous, dicalcium phosphate dihydrate, dicalcium phosphate anhydrous, tetracalcium phosphate, calcium orthophosphate phosphate, calcium pyrophosphate, alpha-tricalcium phosphate, beta-tricalcium phosphate, apatite such as hydroxyapatite, or polymers such as, for example, poly(alpha-hydroxyesters), poly(ortho esters), poly(ether esters), polyanhydrides, poly(phosphazenes), poly(propylene fumarates), poly(ester amides), poly(ethylene fumarates), poly(amino acids), polysaccharides, polypeptides, poly(hydroxy butyrates), poly(hydroxy valerates), polyurethanes, poly(malic acid), polylactides, polyglycolides, polycaprolactones, poly(glycolide-co-trimethylene carbonates), polydioxanones, or copolymers, terpolymers thereof or blends of those polymers, or a combination of biocompatible and biodegradable materials. One can also use biodegradable glass and bioactive glass self-reinforced and ultrahigh strength bioabsorbable composites assembled from partially crystalline bioabsorbable polymers, like polyglycolides, polylactides and/or glycolide/lactide copolymers.

These materials preferably have high initial strength, appropriate modulus and strength retention time from 4 weeks up to 1 year in vivo, depending on the implant geometry. Reinforcing elements such as fibers of crystalline polymers, fibers of carbon in polymeric resins, and particulate fillers, e.g., hydroxyapatite, may also be used to provide the dimensional stability and mechanical properties of biodegradable devices. The use of interpenetrating networks (IPN) in biodegradable material construction has been demonstrated as a means to improve mechanical strength. To further improve the mechanical properties of IPN-reinforced biodegradable materials, the present device may be prepared as semi-interpenetrating networks (SIPN) of crosslinked polypropylene fumarate within a host matrix of poly(lactide-co-glycolide) 85:15 (PLGA) or poly(l-lactide-co-d,l-lactide) 70:30 (PLA) using different crosslinking agents. One can also use natural poly(hydroxybutyrate-co-9% hydroxyvalerate) copolyester membranes as described in Charles-Hilaire Rivard et al. (Journal of Applied Biomaterials, Volume 6 Issue 1, Pages 65-68, 1 Sep. 2004). A skilled artisan will be able to also select other biodegradable materials suitable for any specific purposes and cell and tissue types according to the applications in which the device is used.

The device as described can also be used as therapeutic devices, when placed in vivo. One can re-create organ mimics, such as bone marrow or lymph nodes by placing the devices in, for example an animal model allowing the device to be inhabited by living cells and tissues, and then removing the entire device with living cells while perfusing the vascular channel with medium. The device can then be removed and kept alive ex vivo for in vitro or ex vivo studies. In particular, the membrane may be coated with one or more cell layers on at least one side of the membrane in vitro. In this embodiment, the cells are plated outside an organism. In an embodiment, the membrane is coated with one or more cell layers on at least one side of the membrane in vivo. One can treat one side of the membrane in vitro and the other side in vivo. One can also have one or both sides initially coated with one cell type in vitro and then implant the device to attract additional cell layers in vivo.

In general, the present disclosure is directed to device and method of use in which the device includes a body having a central microchannel separated by one or more porous membranes. The membrane(s) are configured to divide the central microchannel into two or more closely apposed parallel central microchannels, wherein one or more first fluids are applied through the first central microchannel and one or more second fluids are applied through the second or more central microchannels. The surfaces of each porous membrane can be coated with cell adhesive molecules to support the attachment of cells and promote their organization into tissues on the upper and lower surface of the membrane, thereby creating a tissue-tissue interface separated by a porous membrane between the adjacent parallel fluid channels. The membrane may be porous, flexible, elastic, or a combination thereof with pores large enough to only permit exchange of gases and small chemicals, or large enough to permit migration and transchannel passage of large proteins, and whole living cells. Fluid pressure, flow and channel geometry also may be varied to apply a desired fluid shear stress to one or both tissue layers.

In a non-limiting example embodiment, the device is configured to mimic operation of a lung, whereby lung epithelium cells self assemble on one surface of the ECM membrane and lung capillary endothelium cells self assemble on the opposite face of the same porous membrane. The device thereby allows simulation of the structure and function of a functional alveolar-capillary unit that can be exposed to physiological mechanical strain to simulate breathing or to both air-borne and blood-borne chemical, molecular, particulate and cellular stimuli to investigate the exchange of chemicals, molecules, and cells across this tissue-tissue interface through the pores of the membrane. The device impacts the development of in vitro lung models that mimic organ-level responses which are able to be analyzed under physiological and pathological conditions. This system may be used in several applications including, but not limited to, drug screening, drug delivery, vaccine delivery, biodetection, toxicology, physiology and organ/tissue engineering applications.

FIG. 1 illustrates a block diagram of the overall system employing the inventive device in accordance with an embodiment. As shown in FIG. 1, the system 100 includes an organ mimic device 102, one or more fluid sources 104, $104_N$ coupled to the device 102, one or more optional pumps 106 coupled to the fluid source 104 and device 102. One or more CPUs 110 are coupled to the pump 106 and preferably control the flow of fluid in and out of the device 102. The CPU preferably includes one or processors 112 and one or more local/remote storage memories 114. A display 116 is coupled to the CPU 110, and one or more pressure sources 118 are coupled to the CPU 110 and the device 102. The CPU 110 preferably controls the flow and rate of pressurized fluid to the device. It should be noted that although one interface device 102 is shown and described herein, it is contemplated that a plurality of interface devices 102 may be tested and analyzed within the system 100 as discussed below.

As will be discussed in more detail, the organ mimic device 102 preferably includes two or more ports which place the microchannels of the device 102 in communication with the external components of the system, such as the fluid and pressure sources. In particular, the device 102 is coupled to the one or more fluid sources $104_N$ in which the fluid source may contain air, blood, water, cells, compounds, particulates, and/or any other media which are to be delivered to the device 102. In an embodiment, the fluid source 104 provides fluid to one or more microchannels of the device 102 and also preferably receives the fluid which exits the device 102. It is contemplated that the fluid exiting the device 102 may additionally or alternatively be collected in a fluid collector or reservoir 108 separate from the fluid source 104. Thus, it is possible that separate fluid sources 104, $104_N$ respectively provide fluid to and remove fluid from the device 102.

In an embodiment, fluid exiting the device 102 may be reused and reintroduced into the same or different input port through which it previously entered. For example, the device 102 may be set up such that fluid passed through a particular central microchannel is recirculated back to the device and is again run through the same central microchannel. This could be used, for instance, to increase the concentration of an analyte in the fluid as it is recirculated the device. In another example, the device 102 may be set up such that fluid passed through the device and is recirculated back into the device and then subsequently run through another central microchannel. This could be used to change the concentration or makeup of the fluid as it is circulated through another microchannel.

One or more pumps 106 are preferably utilized to pump the fluid into the device 102, although pumps in general are optional to the system. Fluid pumps are well known in the art and are not discussed in detail herein. As will be discussed in more detail below, each microchannel portion is preferably in communication with its respective inlet and/or outlet port, whereby each microchannel portion of allow fluid to flow therethrough.

Each microchannel in the device preferably has dedicated inlet and outlet ports which are connected to respective dedicated fluid sources and/or fluid collectors to allow the flow rates, flow contents, pressures, temperatures and other characteristics of the media to be independently controlled through each central microchannel. Thus, one can also monitor the effects of various stimuli to each of the cell or tissue layers separately by sampling the separate fluid channels for the desired cellular marker, such as changes in gene expression at RNA or protein level.

The cell injector/remover 108 component is shown in communication with the device 102, whereby the injector/remover 108 is configured to inject, remove and/or manipulate cells, such as but not limited to epithelial and endothelial cells, on one or more surfaces of the interface membrane within the device 102 independent of cells introduced into the device via the inlet port(s) 210, 218. For example, blood containing magnetic particles which pull pathogenic cells may be cultured in a separate device whereby the mixture can be later introduced into the system via the injector at a desired time without having to run the mixture through the fluid source 104. In an embodiment, the cell injector/remover 108 is independently controlled, although the injector/remover 108 may be controlled by the CPU 110 as shown in FIG. 1. The cell injector/remover 108 is an optional component and is not necessary.

Although not required, pressure may be applied from the one or more pressure sources 118 to create a pressure differential to cause mechanical movements within the device 102. In an embodiment in which pressures are used with the device, the pressure source 118 is controlled by the CPU 110 to apply a pressure differential within the device to effectively cause one or more membranes (FIGS. 3A-3B) within the device to expand and/or contract in response to the applied pressure differential. In an embodiment, the pressure applied to the device 100 by the pressure source 118 is a positive pressure, depending on the configuration or application of the device. Additionally or alternatively, the pressure applied by the pressure source 118 is a negative pressure, such as vacuum or suction, depending on the configuration or application of the device. The pressure source 118 is preferably controlled by the CPU 110 to apply pressure at set timed intervals or frequencies to the device 102, whereby the timing intervals may be set to be uniform or non-uniform. The pressure source 118 may be controlled to apply uniform pressure in the timing intervals or may apply different pressures at different intervals. For instance, the pressure applied by the pressure source 118 may have a large magnitude and/or be set at a desired frequency to mimic a person running or undergoing exertion. The pressure source 118 may also apply slow, irregular patterns, such as simulating a person sleeping. In an embodiment, the CPU 110 operates the pressure source 118 to randomly vary intervals of applying pressure to cause cyclic stretching patterns to simulate irregularity in breath rate and tidal volumes during natural breathing.

One or more sensors 120 may be coupled to the device 102 to monitor one or more areas within the device 102, whereby the sensors 120 provide monitoring data to the CPU 110. One type of sensor 120 is preferably a pressure sensor which provides data regarding the amount of pressure in one or more operating or central microchannels the device 102. Pressure data from opposing sides of the microchannel walls may be used to calculate real-time pressure differential information between the operating and central microchannels. The monitoring data would be used by the CPU 110 to provide information on the device's operational conditions as well as how the cells are behaving within the device 102 in particular environments in real time. The sensor 120 may be an electrode, have infrared, optical (e.g. camera, LED), or magnetic capabilities or utilize any other appropriate type of technology to provide the monitoring data. For instance, the sensor may be one or more microelectrodes which analyze electrical characteristics across the membrane (e.g. potential difference, resistance, and short circuit current) to confirm the formation of an organized barrier, as well as its fluid/ion transport function across the membrane. It should be noted that the sensor 120 may be external to the device 102 or be integrated within the device 102. It is contemplated that the CPU 110 controls operation of the sensor 120, although it is not necessary. The data is preferably shown on the display 116.

FIG. 2A illustrates a perspective view of the tissue interface device in accordance with an embodiment. In particular, as shown in FIG. 2A, the device 200 (also referred to reference numeral 102) preferably includes a body 202 having a branched microchannel design 203 in accordance with an embodiment. The body 202 may be made of a flexible material, although it is contemplated that the body be alternatively made of a non-flexible material. It should be noted that the microchannel design 203 is only exemplary and not limited to the configuration shown in FIG. 2A. The body 202 is preferably made of a flexible biocompatible polymer, including but not limited to, polydimethyl siloxane (PDMS), or polyimide. It is also contemplated that the body 202 may be made of non-flexible materials like glass, silicon, hard plastic, and the like. Although it is preferred that the interface membrane be made of the same material as the body 202, it is contemplated that the interface membrane be made of a material that is different than the body of the device.

The device in FIG. 2A includes a plurality of ports 205 which will be described in more detail below. In addition, the branched configuration 203 includes a tissue-tissue interface simulation region (membrane 208 in FIG. 2B) where cell behavior and/or passage of gases, chemicals, molecules, particulates and cells are monitored. FIG. 2B illustrates an exploded view of the organ mimic device in accordance with an embodiment. In particular, the outer body 202 of the device 200 is preferably comprised of a first outer body portion 204, a second outer body portion 206 and an intermediary porous membrane 208 configured to be mounted between the first and second outer body portions 204, 206 when the portions 204, 206 are mounted to one another to form the overall body.

FIG. 2B illustrates an exploded view of the device in accordance with an embodiment. As shown in FIG. 2B, the first outer body portion 204 includes one or more inlet fluid ports 210 preferably in communication with one or more corresponding inlet apertures 211 located on an outer surface of the body 202. The device 100 is preferably connected to the fluid source 104 via the inlet aperture 211 in which fluid travels from the fluid source 104 into the device 100 through the inlet fluid port 210.

Additionally, the first outer body portion 204 includes one or more outlet fluid ports 212 preferably in communication with one or more corresponding outlet apertures 215 on the outer surface of the body 202. In particular, fluid passing through the device 100 exits the device 100 to a fluid collector 108 or other appropriate component via the corresponding outlet aperture 215. It should be noted that the device 200 may be set up such that the fluid port 210 is an outlet and fluid port 212 is an inlet. Although the inlet and outlet apertures 211, 215 are shown on the top surface of the body 202, one or more of the apertures may be located on one or more sides of the body.

In an embodiment, the inlet fluid port 210 and the outlet fluid port 212 are in communication with the first central microchannel 250A (see FIG. 3A) such that fluid can dynamically travel from the inlet fluid port 210 to the outlet fluid port 212 via the first central microchannel 250A, independently of the second central microchannel 250B (see FIG. 3A).

It is also contemplated that the fluid passing between the inlet and outlet fluid ports may be shared between the central sections 250A and 250B. In either embodiment, characteristics of the fluid flow, such as flow rate and the like, passing through the central microchannel 250A is controllable independently of fluid flow characteristics through the central microchannel 250B and vice versa.

In addition, the first portion 204 includes one or more pressure inlet ports 214 and one or more pressure outlet ports 216 in which the inlet ports 214 are in communication with corresponding apertures 217 located on the outer surface of the device 100. Although the inlet and outlet apertures are shown on the top surface of the body 202, one or more of the apertures may alternatively be located on one or more sides of the body.

In operation, one or more pressure tubes (not shown) connected to the pressure source 118 (FIG. 1) provides positive or negative pressure to the device via the apertures 217. Additionally, pressure tubes (not shown) are connected to the device 100 to remove the pressurized fluid from the outlet port 216 via the apertures 223. It should be noted that the device 200 may be set up such that the pressure port 214 is an outlet and pressure port 216 is an inlet. It should be noted that although the pressure apertures 217, 223 are shown on the top surface of the body 202, it is contemplated that one or more of the pressure apertures 217, 223 may be located on one or more side surfaces of the body 202.

Referring to FIG. 2B, the second outer body portion 206 preferably includes one or more inlet fluid ports 218 and one or more outlet fluid ports 220. It is preferred that the inlet fluid port 218 is in communication with aperture 219 and outlet fluid port 220 is in communication with aperture 221, whereby the apertures 219 and 221 are preferably located on the outer surface of the second outer body portion 206. Although the inlet and outlet apertures are shown on the surface of the body 202, one or more of the apertures may be alternatively located on one or more sides of the body.

As with the first outer body portion 204 described above, one or more fluid tubes connected to the fluid source 104 (FIG. 1) are preferably coupled to the aperture 219 to provide fluid to the device 100 via port 218. Additionally, fluid exits the device 100 via the outlet port 220 and out aperture 221 to a fluid reservoir/collector 108 or other component. It should be noted that the device 200 may be set up such that the fluid port 218 is an outlet and fluid port 220 is an inlet.

In addition, it is preferred that the second outer body portion 206 includes one or more pressure inlet ports 222 and one or more pressure outlet ports 224. In particular, it is preferred that the pressure inlet ports 222 are in communication with apertures 227 and pressure outlet ports 224 are in communication with apertures 229, whereby apertures 227 and 229 are preferably located on the outer surface of the second portion 206. Although the inlet and outlet apertures are shown on the bottom surface of the body 202, one or more of the apertures may be alternatively located on one or more sides of the body. Pressure tubes connected to the pressure source 118 (FIG. 1) are preferably engaged with ports 222 and 224 via corresponding apertures 227 and 229. It should be noted that the device 200 may be set up such that the pressure port 222 is an outlet and fluid port 224 is an inlet.

Figure 5A:
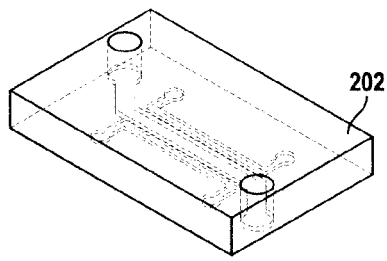
FIGS. 5A-5E illustrate perspective views of the formation of the organ mimic device in accordance with an embodiment.
Figure 5B:
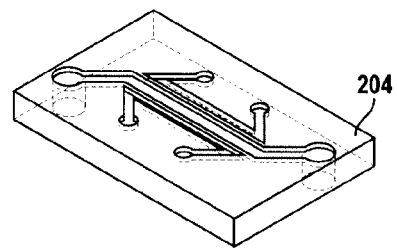
Figure 5C:
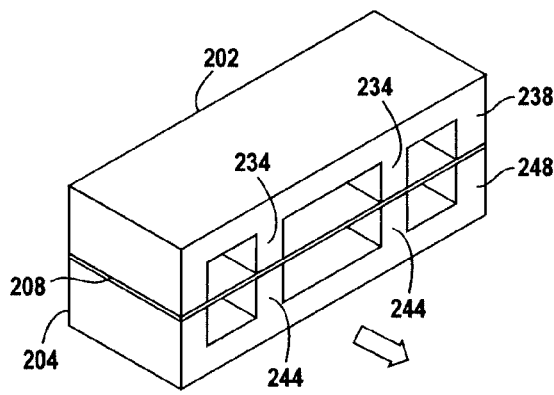
Figure 5D:
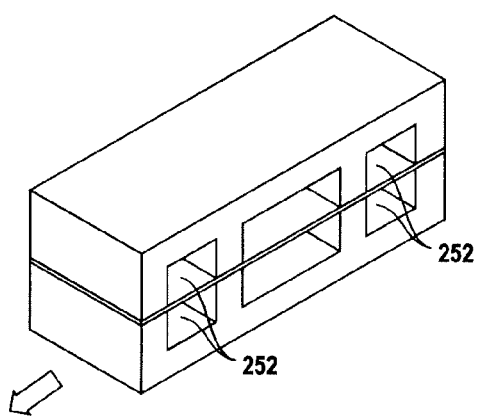
Figure 5E:
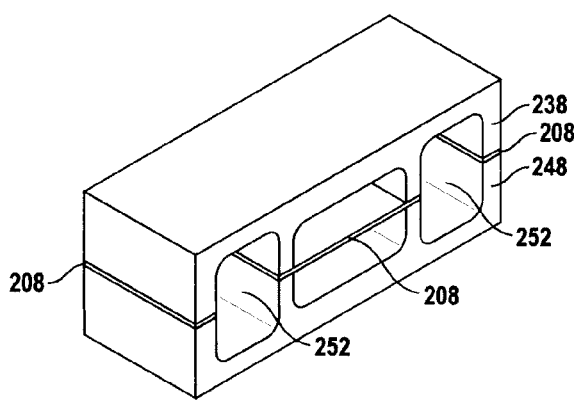

In an embodiment, the membrane 208 is mounted between the first portion 204 and the second portion 206, whereby the membrane 208 is located within the body 202 of the device 200 (see FIG. 5E). In an embodiment, the membrane 208 is a made of a material having a plurality of pores or apertures therethrough, whereby molecules, cells, fluid or any media is capable of passing through the membrane 208 via one or more pores in the membrane 208. As discussed in more detail below, it is contemplated in an embodiment that the porous membrane 208 may be made of a material which allows the membrane 208 to undergo stress and/or strain in response to pressure differentials present between the central microchannels 250A, 250B and the operating microchannels. Alternatively, the porous membrane 208 is relatively inelastic in which the membrane 208 undergoes minimal or no movement while media is passed through one or more of the central microchannels 250A, 250B and cells organize and move between the central microchannels 250A, 250B via the porous membrane.

Referring FIG. 2C illustrates a perspective view of the tissue-tissue interface region of the first outer portion 204 of the body taken at line C-C (from FIG. 2B). As shown in FIG. 2C, the top portion of the tissue-tissue interface region 207A is within the body of the first portion 204 and includes a top portion of a central microchannel 230 and one or more top portion side operating microchannels 232 located adjacent to the central microchannel 230. Microchannel walls 234 preferably separate the central microchannel 230 from the operating microchannels 232 such that fluid traveling through the central microchannel 230 does not pass into operating microchannels 232. Likewise, the channel walls 234 prevent pressurized fluid passing along operating microchannels 232 from entering the central microchannel 230. It should be noted that a pair of operating microchannels 232 are shown on opposing sides of central microchannel 230 in FIGS. 2C and 3A, however it is contemplated that the device may incorporate more than two operating microchannels 232. It is also contemplated that the device 200 may include only one operating microchannel 232 adjacent to the central microchannel 230.

Figure 2D:
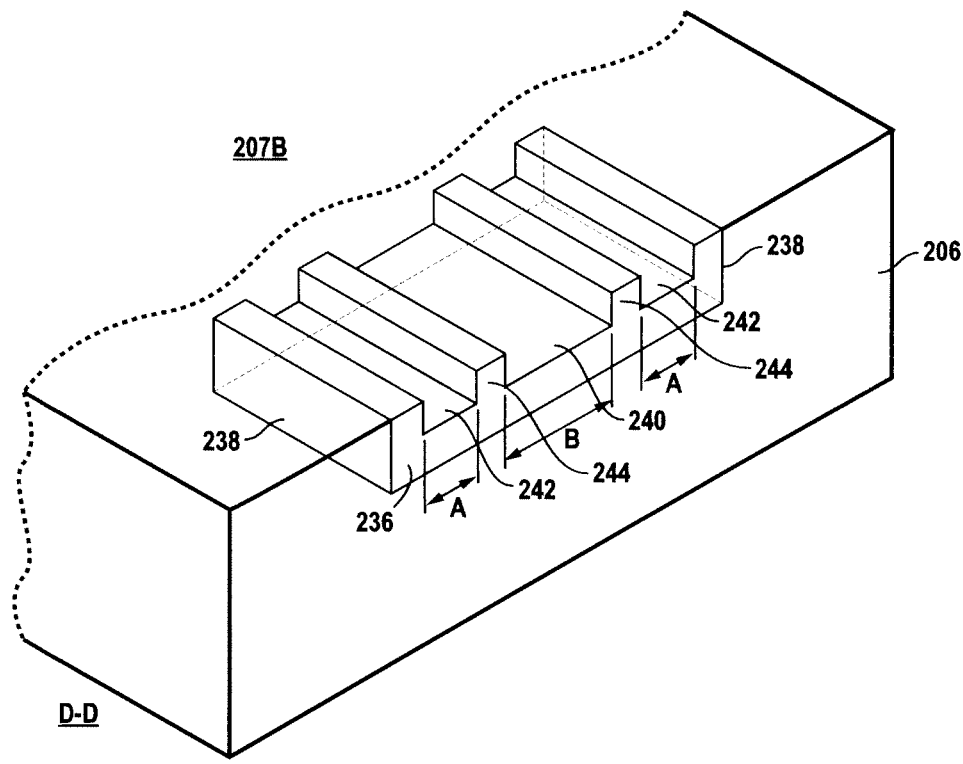

FIG. 2D illustrates a perspective view of the tissue interface region taken at line D-D of the second outer portion 206 of the body. As shown in FIG. 2D, the tissue interface region includes a bottom portion of the central microchannel 240 and at least two bottom portions of operating microchannels 242 located adjacent to the central microchannel 240 portion. A pair of channel walls 234 preferably separate the central microchannel 240 from the operating microchannels 232 such that fluid traveling through the central microchannel 230 does not pass into operating microchannels 232. Likewise, the channel walls 234 prevent pressurized fluid passing along operating microchannels 232 from entering the central microchannel 230.

As shown in FIGS. 2C and 2D, the top and bottom portions 230 and 240 of the central microchannel each have a range of width dimension (shown as B) between 50 and 1000 microns, and preferably around 400 microns. It should be noted that other width dimensions are contemplated depending on the type of physiological system which is being mimicked in the device. Additionally, the top and bottom portions of the operating microchannels 232 and 242 each have a width dimension (shown as A) between 25 and 800 microns, and preferably around 200 microns, although other width dimensions are contemplated. The height dimensions of the central and/or operating microchannels range between 50 microns and several centimeters, and preferably around 200 microns. The microchannel walls 234, 244 preferably have a thickness range between 5 microns to 50 microns, although other width dimensions are contemplated depending on the material used for the walls, application in which the device is used and the like.

FIG. 3A illustrates a perspective view of the tissue interface region within the body in accordance with an embodiment. In particular, FIG. 3A illustrates the first portion 207A and the second portion 207B mated to one another whereby the side walls 228 and 238 as well as channel walls 234, 244 form the overall central microchannel 250 and operating microchannels 252. As stated above, it is preferred that central microchannel 250 and operating microchannels 252 are separated by the walls 234, 244 such that fluid is not able to pass between the channels 250, 252.

The membrane 208 is preferably positioned in the center of the central microchannel 250 and is oriented along a plane parallel to the x-y plane shown in FIG. 3A. It should be noted that although one membrane 208 is shown in the central microchannel 250, more than one membrane 208 may be configured within the central microchannel 250, as discussed in more detail below. In addition to being positioned within the central microchannel 250, the membrane 208 is sandwiched in place by channel walls 234, 244 during formation of the device.

The membrane 208 preferably separates the overall central microchannel 250 into two or more distinct central microchannels 250A and 250B. It should be noted that although the membrane 208 is shown midway through the central microchannel 250, the membrane 208 may alternatively be positioned vertically off-center within the central microchannel 250, thus making one of the central microchannel sections 250A, 250B larger in volume or cross-section than the other microchannel section.

As will be discussed in more detail below, the membrane 208 may have at least a portion which is porous to allow cells or molecules to pass therethrough. Additionally or alternatively, at least a portion of the membrane 208 may have elastic or ductile properties which allow the membrane 208 to be manipulated to expand/contract along one or more planar axe. Thus, it is contemplated that one or more portions of the membrane 208 may be porous and elastic or porous, but inelastic.

With regard to the porous and elastic membrane, a pressure differential may be applied within the device to cause relative continuous expansion and contraction of the membrane 208 along the x-y plane. In particular, as stated above, one or more pressure sources preferably apply pressurized fluid (e.g. air) along the one or more operating microchannels 252, whereby the pressurized fluid in the microchannels 252 creates a pressure differential on the microchannel walls 234, 244. The membrane 208 may have an elasticity depending on the type of material that it is made of. If the membrane 208 is made of more than one material, the weight ratio of the respective materials which make up the membrane is a factor in determining the elasticity. For example, in the embodiment that the membrane 208 is made of PDMS, the Young's modulus values are in the ranges of 12 kPa-20 MPa, although other elasticity values are contemplated.

In the embodiments shown in FIGS. 3A and 3B, the pressurized fluid is a vacuum or suction force that is applied only through the operating microchannels 252. The difference in pressure caused by the suction force against the microchannel walls 234, 244 causes the walls 234, 244 to bend or bulge outward toward the sides of the device 228, 238 (see FIG. 3B). Considering that the membrane 208 is mounted to and sandwiched between the walls 234, 244, the relative movement of the walls 234, 244 thereby causes the opposing ends of the membrane to move along with the walls to stretch (shown as 208' in FIG. 3B) along the membrane's plane. This stretching mimics the mechanical forces experienced by a tissue-tissue interface, for example, in the lung alveolus during breathing, and thus provides the important regulation for cellular self assembly into tissue structures and cell behavior.

When the negative pressure is no longer applied (and/or positive pressure is applied to the operating channels), the pressure differential between the operating channels 252 and the central channel 250 decreases and the channel walls 234, 244 retract elastically toward their neutral position (as in FIG. 3A). During operation, the negative pressure is alternately applied in timed intervals to the device 200 to cause continuous expansion and contraction of the membrane 208 along its plane, thereby mimicking operation of the tissue-tissue interface of the living organ within a controlled in vitro environment. As will be discussed, this mimicked organ operation within the controlled environment allows monitoring of cell behavior in the tissues, as well as passage of molecules, chemicals, particulates and cells with respect to the membrane and the associated first and second microchannels 250A, 250B.

It should be noted that the term pressure differential in the present specification relates to a difference of pressure on opposing sides of a particular wall between the central microchannel and the outer operating channel. It is contemplated that the pressure differential may be created in a number of ways to achieve the goal of expansion and/or contraction of the membrane 208. As stated above, a negative pressure (i.e. suction or vacuum) may be applied to one or more of the operating channels 252. Alternatively, it is contemplated that the membrane 208 is pre-loaded or pre-stressed to be in an expanded state by default such that the walls 234, 244 are already in the bent configuration, as show in FIG. 3B. In this embodiment, positive pressure applied to the operating channel 252 will create the pressure differential which causes the walls 234, 244 to move inward toward the central microchannel (see in FIG. 3A) to contract the membrane 208.

It is also contemplated, in another embodiment, that a combination of positive and negative pressure is applied to one or more operating microchannels 252 to cause movement of the membrane 208 along its plane in the central microchannel. In any of the above embodiments, it is desired that the pressure of the fluid in the one or more operating channels 252 be such that a pressure differential is in fact created with respect to the pressure of the fluid(s) in one or more of the central microchannel(s) 250A, 250B to cause relative expansion/contraction of the membrane 208. For example, fluid may have a certain pressure may be applied within the top central microchannel 250A, whereby fluid in the bottom central microchannel 250B may have a different pressure. In this example, pressure applied to the one or more operating channels 252 must take into account the pressure of the fluid in either or both of the central microchannels 250A, 250B to ensure desired expansion/contraction of the membrane 208.

It is possible, in an embodiment, for a pressure differential to exist between the top and bottom microchannels 250A, 250B to cause at least a portion of the membrane 208 to expand and/or contract vertically in the z-direction in addition to expansion/contraction along the x-y plane.

In an embodiment, the expansion and retraction of the membrane 208 preferably applies mechanical forces to the adherent cells and ECM that mimic physiological mechanical cues that can influence transport of chemicals, molecules particulates, and/or fluids or gas across the tissue-tissue interface, and alter cell physiology. It should be noted that although pressure differentials created in the device preferably cause expansion/contraction of the membrane, it is contemplated that mechanical means, such as micromotors or actuators, may be employed to assist or substitute for the pressure differential to cause expansion/contraction of the cells on the membrane to modulate cell physiology.

Figure 4A:
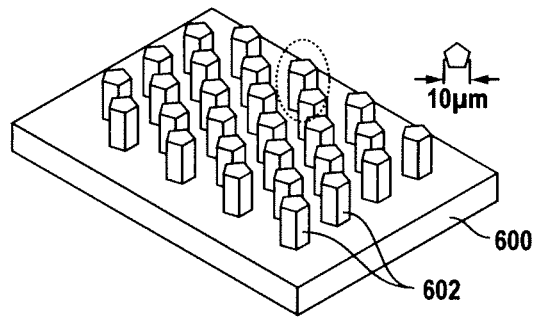
FIGS. 4A-4C illustrate perspective views of the formation of the membrane of a two channel device in accordance with an embodiment.
Figure 4B:
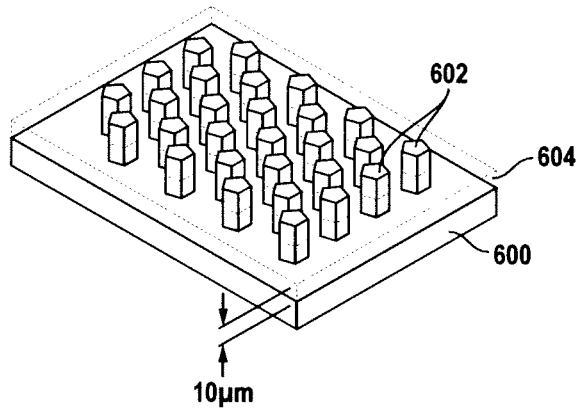
Figure 4C:
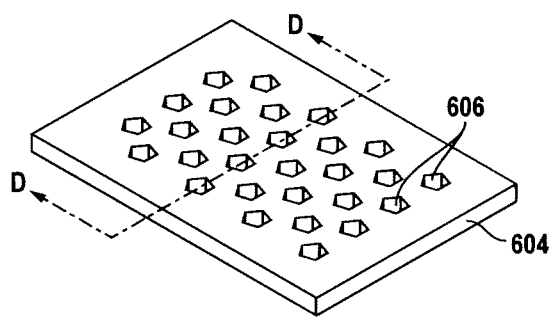

FIGS. 3E and 4C illustrate perspectives view of the membrane 208 which includes a plurality of apertures 302 extending therethrough in accordance with an embodiment. In particular, the membrane shown in FIGS. 3E and 4C includes one or more of integrated pores or apertures 302 which extend between a top surface 304 and a bottom surface 306 of the membrane 208.

The membrane is configured to allow cells, particulates, chemicals and/or media to migrate between the central microchannel portions 250A, 250B via the membrane 208 from one section of the central microchannel to the other or vice versa. The pore apertures are shown to have a pentagonal cross sectional shape in FIGS. 4A-4C, although any other cross sectional shape is contemplated, including but not limited to, a circular shaped 302, hexagonal 308, square, elliptical 310 and the like. The pores 302, 308, 310 (generally referred to as reference numeral 302) preferably extend vertically between the top and bottom surfaces 304, 306, although it is contemplated that they may extend laterally as well between the top and bottom surfaces, as with pore 312. It should also be noted that the porous may additionally/alternatively incorporate slits or other shaped apertures along at least a portion of the membrane 208 which allow cells, particulates, chemicals and/or fluids to pass through the membrane 208 from one section of the central microchannel to the other.

The width dimension of the pores are preferably in the range of 0.5 microns and 20 microns, although it is preferred that the width dimension be approximately 10 microns. It is contemplated, however, that the width dimension be outside of the range provided above. In some embodiments, the membrane 208 has pores or apertures larger than traditional molecular/chemical filtration devices, which allow cells as well as molecules to migrate across the membrane 208 from one microchannel section (e.g. 250A) to the other microchannel section (e.g. 250B) or vice versa. This may be useful in culturing cells which polarize in the top and bottom central channels in response to being in the microchannel environment provided by the device whereby fluid(s) and cells are dynamically passed through pores that connect these microchannels 250A, 250B.

As shown in FIG. 4B, the thickness of the membrane 208 may be between 70 nanometers and 50 microns, although a preferred range of thickness would between 5 and 15 microns. It is also contemplated that the membrane 208 be designed to include regions which have lesser or greater thicknesses than other regions in the membrane 208. As shown in FIG. 3C, the membrane 208 is shown to have one or more decreased thickness areas 209 relative to the other areas of the membrane 208. The decreased thickness area(s) 209 may run along the entire length or width of the membrane 208 or may alternatively be located at only certain locations of the membrane 208. It should be noted that although the decreased thickness area 209 is shown along the bottom surface of the membrane 208 (i.e. facing microchannel 250B), it is contemplated that the decreased thickness area(s) 209 may additionally/alternatively be on the opposing surface of the membrane 208 (i.e. facing microchannel 250A). It should also be noted that at least portions of the membrane 208 may have one or more larger thickness areas 209' relative to the rest of the membrane, as shown in FIG. 3D and capable of having the same alternatives as the decreased thickness areas described above.

In an embodiment, the porous membrane 208 may be designed or surface patterned to include micro and/or nanoscopic patterns therein such as grooves and ridges, whereby any parameter or characteristic of the patterns may be designed to desired sizes, shapes, thicknesses, filling materials, and the like.

In an embodiment, the membrane 208 is made of polydimethylsiloxane (PDMS) or any other polymeric compound or material, although this is not necessary. For instance, the membrane 208 may be made of polyimide, polyester, polycarbonate, cyclicolefin copolymer, polymethylmethacrylate, nylon, polyisoprene, polybutadiene, polychlorophene, polyisobutylene, poly(styrene-butadiene-styrene), nitriles, the polyurethanes and the polysilicones. GE RTV 615, a vinylsilane crosslinked (type) silicone elastomer (family) may be used. Polydimethysiloxane (PDMS) membranes are available HT-6135 and HT-6240 membranes from Bisco Silicons (Elk Grove, Ill.) and are useful in selected applications. The choice of materials typically depends upon the particular material properties (e.g., solvent resistance, stiffness, gas permeability, and/or temperature stability) required for the application being conducted. Additional elastomeric materials that can be used in the manufacture of the components of the microfluidic devices described in Unger et al., (2000 Science 288:113-116). Some elastomers of the present devices are used as diaphragms and in addition to their stretch and relax properties, are also selected for their porosity, impermeability, chemical resistance, and their wetting and passivating characteristics. Other elastomers are selected for their thermal conductivity. Micronics Parker Chomerics Thermagap material 61-02-0404-F574 (0.020" thick) is a soft elastomer (<5 Shore A) needing only a pressure of 5 to 10 psi to provide a thermal conductivity of 1.6 W/m-° K. Deformable films, lacking elasticity, can also be used in the microfluidic device. One may also use silk, ECM gels with or without crosslinking as other such suitable materials to make the devices and membranes as described.

It should be noted that although the central and operating microchannels 250, 252 are shown to have substantially square or rectangular cross sections, other cross-sectional shapes are contemplated such as circular, oval, hexagonal, and the like. It is also contemplated that the device 200 may have more or less than two operating channels 252 and/or more or less than two central microchannels 250A, 250B in accordance with an embodiment.

Figure 2E:
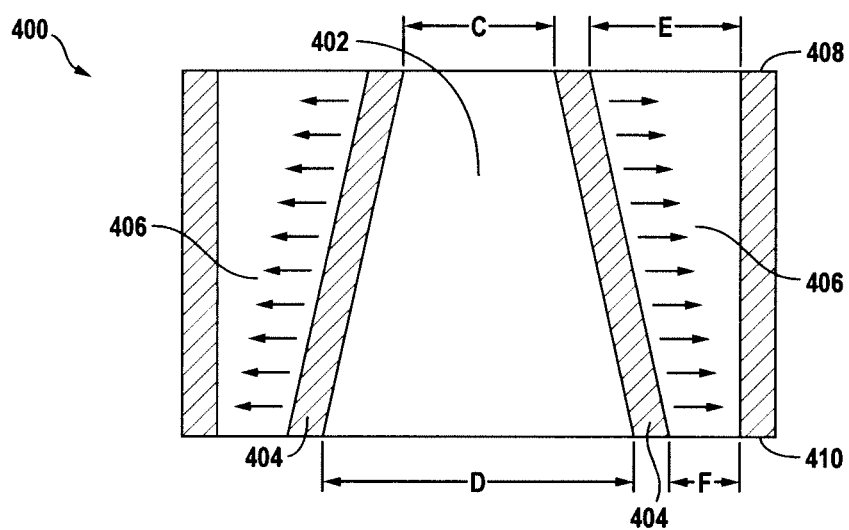
FIGS. 2E-2G illustrate top down cross sectional views of the tissue-tissue interface regions of the device in accordance with one or more embodiments.
Figure 2F:
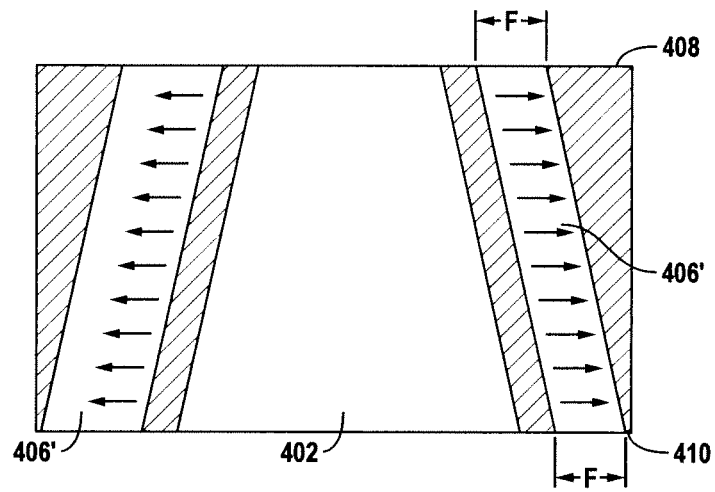

In an embodiment, it is contemplated that the central microchannel has a non-uniform width dimension B along at least a portion of its length in the device. FIG. 2E illustrates a cross sectional top-down view of the tissue interface region 400 in accordance with an embodiment. As shown in FIG. 2E, the interface 400 includes the central microchannel 402 along with adjacent operating channels 406 separated by microchannel walls 404. In the embodiment in FIG. 2E, the central microchannel 402 is shown to have a gradually increasing width from width dimension C (at end 408) to width dimension D (at end 410). In the embodiment in FIG. 2E, the operating channels 406 each have a correspondingly decreasing width dimension (from width dimension E at end 408 to width dimension F at end 410). In another embodiment, as shown in FIG. 2F, the operating channels 406' have a substantially uniform width dimension F at ends 408 and 410. It is contemplated that the membrane (not shown) be placed above the central microchannel 402 and mounted to the top surface of the walls 404, whereby the membrane has a tapered shape similar to the central microchannel 402. The tapered membrane would thereby undergo non-uniform stretching in the direction of the arrows when the pressure differential is applied between the operating microchannels 406 and the central microchannel 402.

Figure 2G:
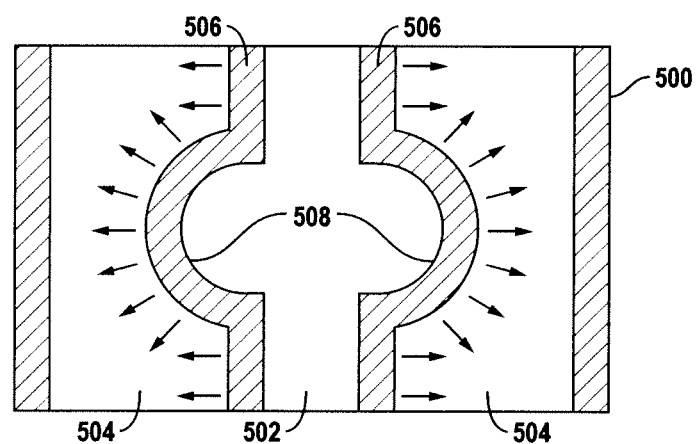

In another embodiment, the central microchannel may have a portion which has a partially circular cross sectional shape, as shown in FIG. 2G. In particular to the embodiment in FIG. 2G, a pressure differential created between the central microchannel 502 and the adjacent operating microchannels 504 will cause the microchannel walls 506 to move in the direction represented by the arrows. With regard to the circular portion 508 of the central microchannel 502, equiaxial outward movement of the walls (as shown by the arrows) at the central portion 508 produces equiaxial stretching of the membrane (not shown) mounted atop of the walls 506.

The device 200 described herein has potential for several applications. For example, in one application, the membrane 208 may be subjected to physiological mechanical strain generated by cyclic stretching of the membrane 208 and/or the flow of biological fluids (e.g. air, mucus, blood) to recapitulate the native microenvironment of the alveoli and underlying pulmonary capillaries. In an embodiment, the culture conditions of cells upon the membrane 208 may be optimized under extracellular matrix (ECM) coating, media perfusion, or cyclic mechanical strain to maintain morphological and functional characteristics of the co-cultured cells and to permit their direct cellular interaction across the membrane 208. The device 200 would thus permit long-term cell culture and dynamic mechanical stretching of a adjacent monolayers of lung epithelial or endothelial cells grown on the membrane at the same time.

In utilizing the membrane 208 in simulating the tissue-tissue interface between the alveolar epithelium and pulmonary endothelium in the lung, one method may be to apply type I alveolar epithelial cells to the side of the membrane 208 facing the first section 250A (hereinafter top side of membrane) to mimic the epithelial layer. It is possible, however, to mix type I-like and type II-like alveolar epithelial cells at a ratio of approximately 7:13 to reconstruct the in vivo cellular composition of the alveolar epithelium. In the example method, lung microvascular endothelial cells are cultured on the opposite side of the membrane 208 facing the second section 250B (hereinafter bottom side of membrane). In the example method, negative pressure is cyclically applied to the device 200 to cause the membrane 208 to continuously expand and contract along its plane.

During such operation, a physiological alveolar-capillary unit may be formed on the membrane 208 since typical junctional structures may form on the membrane 207 and fluids as well as ions be transported across the membrane 208 between the first and second sections 250A, 250B. The formation of tight junctions on the membrane 208 may be evaluated using on-chip immunohistochemical detection of tight junction proteins such as ZO-1 and occludin. Additionally or alternately, the exclusion of fluorescently labeled large molecules (e.g. dextrans of different weight) may be quantitated to determine the permeability of the membrane and optimize epithelial membrane barrier formation by varying culture conditions. Additionally, histological, biochemical, and microfluorimetric techniques may be employed to demonstrate formation of a functional alveolar-capillary unit that reproduces the key structural organization of its in vivo counterpart on the membrane 208.

In an example, the gas exchange function of the tissue-tissue interface self assembled on membrane 208 may be determined by injecting different fluids, each having their own oxygen partial pressures and blood, into the respective first and second sections 250A, 250B, whereby the first section 250A acts as the alveolar compartment and the second section 250B acts as the microvascular compartment. A blood-gas measurement device preferably within the device 200 is used to measure the level of oxygen in the blood in the respective sections 250A, 250B before and after the passing of the blood through the device. For example, blood can flow through the channel 250B while air is being injected into the upper channel 250A, whereby the exiting air is collected and measured to determine the oxygen level using an oximeter. Oximeters can be integrated with the existing system or as a separate unit connected to the outlet port of one or more central microchannels. In an embodiment, air or another medium with aerosols containing drugs or particulates may flow through the device, whereby the transport of these drugs or particulates to the blood via the membrane is then measured. It is also contemplated that pathogens or cytokines are added to the air or gaseous medium side and then the sticking of immune cells to nearby capillary endothelium and their passage along with edema fluid from the blood side to the airway side, as well as pathogen entry into blood, are measured.

Since the functionality of an epithelium requires polarization of constituent cells, the structure of the membrane may be visualized using transmission electron microscopy, immunohistocytochemistry, confocal microscopy, or other appropriate means to monitor the polarization of the alveolar epithelial cell side of the membrane 208. In a lung mimic embodiment, a fluorescent dye may be applied to the first and/or second microchannels 250A, 250B to determine pulmonary surfactant production by the airway epithelium at the membrane 208. In particular, alveolar epithelial cells on the membrane 208 can be monitored by measuring the fluorescence resulting from cellular uptake of the fluorescence dye that specifically labels intracellular storage of pulmonary surfactant (e.g. quinacrine) or using specific antibodies.

One of the unique capabilities of the tissue interface device 200 allows development of in vitro models that simulate inflammatory responses of the lung at the organ level to allow study of how immune cells migrate from the blood, through the endothelium and into the alveolar compartment. One way this is achieved is by controlled and programmable microfluidic delivery of pro-inflammatory factors (e.g. IL-1β, TNF-α, IL-8, silica micro- and nanoparticles, pathogens) to the first section 250A as well as whole human blood flowing or medium containing circulating immune cells in the second section 250B. Electrical resistance and short circuit current across the membrane may be monitored to study changes in the vascular permeability, extravasation of fluid and cell passage into the alveolar space during inflammatory responses. Fluorescence microscopy can be used to visualize dynamic cell motile behavior during the extravasation response.

The tissue interface device 200 may also be used to examine how nanomaterials behave with respect to the lung tissue-tissue interface. In particular, nanomaterials (e.g. silica nanoparticles, superparamagnetic nanoparticles, gold nanoparticles, single-walled carbon nanotubes) may be applied to the airway surface of the membrane 208 to investigate potential toxic effects of nanomaterials on airway or endothelial cells grown on the membrane 208, as well as their passage from the airway channel into the blood channel. For instance, sensors 120 can be used to monitor transmigration of nanomaterials through tissue barriers formed on the membrane 208 and nanomaterial-induced changes in barrier functions such as gas exchange and fluid/ion transport.

The tissue interface device 200 permits direct analysis of a variety of important areas of lung biology and physiology including but not limited to gas exchange, fluid/ion transport, inflammation, infection, edema/respiratory distress syndrome, cancer and metastasis development, fungal infection, drug delivery as well as drug screening, biodetection, and pulmonary mechanotransduction. In addition, the device 200 allows for accurately modeling biological tissue-tissue interfaces found in other physiological systems such as the blood-brain barrier, intestine, bone marrow, glomerulus, and cancerous tumor microenvironment. As stated above, more than one tissue interface device 200 may be multiplexed and automated to provide high-throughput analysis of cell and tissue responses to drugs, chemicals, particulates, toxins, pathogens or other environmental stimuli for drug, toxin and vaccine screening, as well as toxicology and biodetection applications. The device may be used for studying complex tissue and organ physiology in vitro, as well as tissue and organ engineering in vivo with biocompatible or biodegradeable devices.

In an embodiment, the tissue interface device 200 can be used to produce artificial tissue layers therein. In the embodiment, two or more different types of cells are applied on opposing surfaces of the membrane 208 and grown under conditions that mimic the appropriate physiological environments. Additionally or alternatively, a pressure differential can be applied between the central microchannel and at least one of the operating microchannels which causes the microchannel walls to move and thus causes the membrane 208 to undergo expansion/contraction along its plane.

In another example, the device 200 utilizes the porous membrane 208, whereby lung cells are grown on one side of the membrane 208 and endothelial cells are maintained on the other side of the membrane 208. During the operation of the device 200, these two cells layers communicate with each other through passage of chemical and molecular cues through the pores on the membrane 208. This communication may be monitored and analyzed to understand how the cells function differently as a tissue-tissue interface, with or without physiological mechanical simulation, and compared to when grown as single tissue types in isolation as in standard tissue culture systems. By monitoring changes in cell and tissue physiology, as well as passage of chemicals, molecules, particulates and cells across this tissue-tissue interface, information is obtained which may be used to produce more effective drugs or therapies, to identify previously unknown toxicities, and to significantly shorten the timescale of these development processes. In particular, the behavior of cells in such a controlled environment allows researchers to study a variety of physiological phenomena taking place in the systems mentioned above that can not be recreated using conventional in vitro culture techniques. In other words, the device 200 functions to create a monitorable artificial blood-air barrier outside a patient's body and in a controllable environment that still retains key physiological functions and structures of the lung. It should be noted that although the device above is described in terms of mimicking lung function, the device may easily be configured to mimic other physiological systems such as peristalsis and absorption in the gastrointestinal tract containing living microbial populations, perfusion and urine production in the kidney, function of the blood-brain barrier, effects of mechanical deformation on skin aging, bone marrow-microvessel interface with hematopoietic stem cell niche, and the like.

Figure 4D:
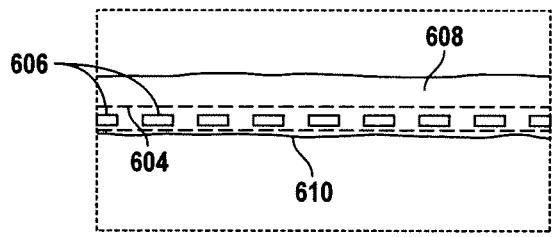
FIG. 4D illustrates a side view of the membrane of the tissue-tissue interface device in accordance with an embodiment.

Details of membrane surface treatment and types of media which can be applied to the membrane and/or through the central microchannels 250A, 250B in operating the device will now be discussed. The membrane including the porous membrane can be coated with substances such as various cell adhesion promoting substances or ECM proteins, such as fibronectin, laminin or various collagen types or combinations thereof, as shown in FIG. 4D. In general, as shown in FIG. 4D, one or more substances 608 is shown on one surface of the membrane 604 whereas another substance 610 is applied to the opposing surface of the membrane 604, or both surfaces can be coated with the same substance. In some embodiments, the ECMs, which may be ECMs produced by cells, such as primary cells or embryonic stem cells, and other compositions of matter are produced in a serum-free environment.

In an embodiment, one coats the membrane with a combination of a cell adhesion factor and a positively-charged molecule that are bound to the membrane to improve cell attachment and stabilize cell growth. The positively charged molecule can be selected from the group consisting of polylysine, chitosan, poly(ethyleneimine) or acrylics polymerized from acrylamide or methacrylamide and incorporating positively-charged groups in the form of primary, secondary or tertiary amines, or quaternary salts. The cell adhesion factor can be added to the membrane and is preferably fibronectin, laminin, collagen, vitronectin or tenascin, or fragments or analogs having a cell binding domain thereof. The positively-charged molecule and the cell adhesion factor can be covalently bound to the membrane. In another embodiment, the positively-charged molecule and the cell adhesion factor are covalently bound to one another and either the positively-charged molecule or the cell adhesion factor is covalently bound to the membrane. Also, the positively-charged molecule or the cell adhesion factor or both cam be provided in the form of a stable coating non-covalently bound to the membrane.

In an embodiment, the cell attachment-promoting substances, matrix-forming formulations, and other compositions of matter are sterilized to prevent unwanted contamination. Sterilization may be accomplished, for example, by ultraviolet light, filtration, or heat. Antibiotics may also be added, particularly during incubation, to prevent the growth of bacteria, fungi and other undesired micro-organisms. Such antibiotics include, by way of non-limiting example, gentamicin, streptomycin, penicillin, amphotericin and ciprofloxacin.

In another embodiment, the membrane is coated with cell cultures, including without limitation, primary cell cultures, established cell lines, or stem cell cultures, such as ESC, attached to ECM substances that comprise or consist essentially of fibronectin or collagen.

In an embodiment, the primary cells or cell lines attached to the membrane may be alveolar cells, endothelial cells, intestinal cells, keratinocytes, which include without limitation, human dermal keratinocytes, or any other type of cell listed elsewhere in this specification or well known to one skilled in the art. In other embodiments, the primary cells may be fibroblast cells, which include without limitation, human fetal fibroblast cells. In some embodiments, the stem cells of the stem cell cultures are embryonic stem cells. The source of embryonic stem cells can include without limitation mammals, including non-human primates and humans. Non-limiting examples of human embryonic stem cells include lines BG01, BG02, BG03, BG01v, CHA-hES-1, CHA-hES-2, FCNCBS1, FCNCBS2, FCNCBS3, H1, H7, H9, H13, H14, HSF-1, H9.1, H9.2, HES-1, HES-2, HES-3, HES-4, HES-5, HES-6, hES-1-2, hES-3-0, hES-4-0, hES-5-1, hES-8-1, hES-8-2, hES-9-1, hES-9-2, hES-101, hICM8, hICM9, hICM40, hICM41, hICM42, hICM43, HSF-6, HUES-1, HUES-2, HUES-3, HUES-4 HUES-5, HUES-6, HUES-7 HUES-8, HUES-9, HUES-10, HUES-11, HUES-12, HUES-13, HUES-14, HUESS-15, HUES-16, HUES-17, 13, 14, 16, 13.2, 13.3, 16.2, J3, J3.2, MB01, MB02, MB03, Miz-hES1, RCM-1, RLS ES05, RLS ES 07, RLS ES 10, RLS ES13, RLS ES15, RLS ES 20, RLS ES 21, SA01, SA02, and SA03. In an embodiment, the stem cells of the stem cell cultures are induced pluripotent stem cells.

In an embodiment, the cell cultures may be cell cultures such as primary cell cultures or stem cell cultures which are serum-free. In some these embodiments, a serum-free primary cell ECM is used in conjunction with a primary cell serum-free medium (SFM). Suitable SFM include without limitation (a) EPILIFE® Serum Free Culture Medium supplemented with EPILIFE® Defined Growth Supplement and (b) Defined Keratinocyte-SFM supplemented with Defined Keratinocyte-SFM Growth Supplement, all commercially available from Gibco/Invitrogen (Carlsbad, Calif., US). In some of these embodiments, a serum-free stem cell ECM is used in conjunction with stem cell SFM. Suitable SFM include without limitation STEMPRO® hESC Serum Free Media (SFM) supplemented with basic fibroblast growth factor and .beta.-mercaptoethanol, KNOCKOUT™. D-MEM supplemented with KNOCKOUT™. Serum Replacement (SR), STEMPRO®. MSC SFM and STEMPRO®. NSC SFM, all commercially available from Gibco/Invitrogen (Carlsbad, Calif., US).

In an embodiment, the compositions can also be xeno-free. A composition of matter is said to be "xeno-free" when it is devoid of substances from any animal other than the species of animal from which the cells are derived. In an embodiment, the cell cultures which may be cell cultures such as primary cell cultures or stem cell cultures are xeno-free. In these embodiments, a xeno-free ECM which may be an ECM such as a primary cell ECM or ECM designed specifically to support stem cell growth or differentiation. These matrices may be specifically designed to be xeno-free.

In an embodiment, the cell cultures are primary cells or stem cells cultured in a conditioned culture medium. In other embodiments, the culture medium is an unconditioned culture medium.

In an embodiment, the cell culture conditions are completely defined. In these embodiments, one uses a completely defined cell culture medium in the fluid chambers. Suitable media include without limitation, for primary cells, EPILIFE®. Serum Free Culture Medium supplemented with EPILIFE®. Defined Growth Supplement, and, for stem cells, STEMPRO®. hESC SFM, all commercially available from Gibco/Invitrogen, Carlsbad, Calif., US.

To study the effects of pharmaceuticals, environmental stressors, pathogens, toxins and such, one can add these into the desired cell culture medium suitable for growing the cells attached to the porous membrane in the channel. Thus, one can introduce pathogens, such as bacteria, viruses, aerosols, various types of nanoparticles, toxins, gaseous substances, and such into the culture medium which flows in the chambers to feed the cells.

A skilled artisan will also be able to control the pH balance of the medium according to the metabolic activity of the cells to maintain the pH in a suitable level for any cell or tissue type in question. Monitors and adjustment systems to monitor and adjust pH may be inserted into the device.

The membrane is preferably coated on one or both sides with cells, molecules or other matter, whereby the device provides a controlled environment to monitor cell behavior along and/or between the microchannels via the membrane. One can use any cells from a multicellular organisms in the device. For example, human body comprises at least 210 known types of cells. A skilled artisan can easily construct useful combinations of the cells in the device. Cell types (e.g., human) which can be used in the devices include, but are not limited to cells of the integumentary system including but not limited to Keratinizing epithelial cells, Epidermal keratinocyte (differentiating epidermal cell), Epidermal basal cell (stem cell), Keratinocyte of fingernails and toenails, Nail bed basal cell (stem cell), Medullary hair shaft cell, Cortical hair shaft cell, Cuticular hair shaft cell, Cuticular hair root sheath cell, Hair root sheath cell of Huxley's layer, Hair root sheath cell of Henle's layer, External hair root sheath cell, Hair matrix cell (stem cell); Wet stratified barrier epithelial cells, such as Surface epithelial cell of stratified squamous epithelium of cornea, tongue, oral cavity, esophagus, anal canal, distal urethra and vagina, basal cell (stem cell) of epithelia of cornea, tongue, oral cavity, esophagus, anal canal, distal urethra and vagina, Urinary epithelium cell (lining urinary bladder and urinary ducts); Exocrine secretory epithelial cells, such as Salivary gland mucous cell (polysaccharide-rich secretion), Salivary gland serous cell (glycoprotein enzyme-rich secretion), Von Ebner's gland cell in tongue (washes taste buds), Mammary gland cell (milk secretion), Lacrimal gland cell (tear secretion), Ceruminous gland cell in ear (wax secretion), Eccrine sweat gland dark cell (glycoprotein secretion), Eccrine sweat gland clear cell (small molecule secretion), Apocrine sweat gland cell (odoriferous secretion, sex-hormone sensitive), Gland of Moll cell in eyelid (specialized sweat gland), Sebaceous gland cell (lipid-rich sebum secretion), Bowman's gland cell in nose (washes olfactory epithelium), Brunner's gland cell in duodenum (enzymes and alkaline mucus), Seminal vesicle cell (secretes seminal fluid components, including fructose for swimming sperm), Prostate gland cell (secretes seminal fluid components), Bulbourethral gland cell (mucus secretion), Bartholin's gland cell (vaginal lubricant secretion), Gland of Littre cell (mucus secretion), Uterus endometrium cell (carbohydrate secretion), Isolated goblet cell of respiratory and digestive tracts (mucus secretion), Stomach lining mucous cell (mucus secretion), Gastric gland zymogenic cell (pepsinogen secretion), Gastric gland oxyntic cell (hydrochloric acid secretion), Pancreatic acinar cell (bicarbonate and digestive enzyme secretion), pancreatic endocrine cells, Paneth cell of small intestine (lysozyme secretion), intestinal epithelial cells, Types I and II pneumocytes of lung (surfactant secretion), and/or Clara cell of lung.

One can also coat the membrane with Hormone secreting cells, such as endocrine cells of the islet of Langerhands of the pancreas, Anterior pituitary cells, Somatotropes, Lactotropes, Thyrotropes, Gonadotropes, Corticotropes, Intermediate pituitary cell, secreting melanocyte-stimulating hormone; and Magnocellular neurosecretory cells secreting oxytocin or vasopressin; Gut and respiratory tract cells secreting serotonin, endorphin, somatostatin, gastrin, secretin, cholecystokinin, insulin, glucagon, bombesin; Thyroid gland cells such as thyroid epithelial cell, parafollicular cell, Parathyroid gland cells, Parathyroid chief cell, Oxyphil cell, Adrenal gland cells, chromaffin cells secreting steroid hormones (mineralcorticoids and gluco corticoids), Leydig cell of testes secreting testosterone, Theca interna cell of ovarian follicle secreting estrogen, Corpus luteum cell of ruptured ovarian follicle secreting progesterone, Granulosa lutein cells, Theca lutein cells, Juxtaglomerular cell (renin secretion), Macula densa cell of kidney, Peripolar cell of kidney, and/or Mesangial cell of kidney.

Additionally or alternatively, one can treat at least one side of the membrane with Metabolism and storage cells such as Hepatocyte (liver cell), White fat cell, Brown fat cell, Liver lipocyte. One can also use Barrier function cells (Lung, Gut, Exocrine Glands and Urogenital Tract) or Kidney cells such as Kidney glomerulus parietal cell, Kidney glomerulus podocyte, Kidney proximal tubule brush border cell, Loop of Henle thin segment cell, Kidney distal tubule cell, and/or Kidney collecting duct cell.

Other cells that can be used in the device include Type I pneumocyte (lining air space of lung), Pancreatic duct cell (centroacinar cell), Nonstriated duct cell (of sweat gland, salivary gland, mammary gland, etc.), principal cell, Intercalated cell, Duct cell (of seminal vesicle, prostate gland, etc.), Intestinal brush border cell (with microvilli), Exocrine gland striated duct cell, Gall bladder epithelial cell, Ductulus efferens nonciliated cell, Epididymal principal cell, and/or Epididymal basal cell.

One can also use Epithelial cells lining closed internal body cavities such as Blood vessel and lymphatic vascular endothelial fenestrated cell, Blood vessel and lymphatic vascular endothelial continuous cell, Blood vessel and lymphatic vascular endothelial splenic cell, Synovial cell (lining joint cavities, hyaluronic acid secretion), Serosal cell (lining peritoneal, pleural, and pericardial cavities), Squamous cell (lining perilymphatic space of ear), Squamous cell (lining endolymphatic space of ear), Columnar cell of endolymphatic sac with microvilli (lining endolymphatic space of ear), Columnar cell of endolymphatic sac without microvilli (lining endolymphatic space of ear), Dark cell (lining endolymphatic space of ear), Vestibular membrane cell (lining endolymphatic space of ear), Stria vascularis basal cell (lining endolymphatic space of ear), Stria vascularis marginal cell (lining endolymphatic space of ear), Cell of Claudius (lining endolymphatic space of ear), Cell of Boettcher (lining endolymphatic space of ear), Choroid plexus cell (cerebrospinal fluid secretion), Pia-arachnoid squamous cell, Pigmented ciliary epithelium cell of eye, Nonpigmented ciliary epithelium cell of eye, and/or Corneal endothelial cell.

The following cells can be used in the device by adding them to the surface of the membrane in culture medium. These cells include cells such as Ciliated cells with propulsive function such as Respiratory tract ciliated cell, Oviduct ciliated cell (in female), Uterine endometrial ciliated cell (in female), Rete testis ciliated cell (in male), Ductulus efferens ciliated cell (in male), and/or Ciliated ependymal cell of central nervous system (lining brain cavities).

One can also plate cells that secrete specialized ECMs, such as Ameloblast epithelial cell (tooth enamel secretion), Planum semilunatum epithelial cell of vestibular apparatus of ear (proteoglycan secretion), Organ of Corti interdental epithelial cell (secreting tectorial membrane covering hair cells), Loose connective tissue fibroblasts, Corneal fibroblasts (corneal keratocytes), Tendon fibroblasts, Bone marrow reticular tissue fibroblasts, Other nonepithelial fibroblasts, Pericyte, Nucleus pulposus cell of intervertebral disc, Cementoblast/ cementocyte (tooth root bonelike cementum secretion), Odontoblast/odontocyte (tooth dentin secretion), Hyaline cartilage chondrocyte, Fibrocartilage chondrocyte, Elastic cartilage chondrocyte, Osteoblast/osteocyte, Osteoprogenitor cell (stem cell of osteoblasts), Hyalocyte of vitreous body of eye, Stellate cell of perilymphatic space of ear, Hepatic stellate cell (Ito cell), and/or Pancreatic stellate cell.

Additionally or alternatively, contractile cells, such as Skeletal muscle cells, Red skeletal muscle cell (slow), White skeletal muscle cell (fast), Intermediate skeletal muscle cell, nuclear bag cell of muscle spindle, nuclear chain cell of muscle spindle, Satellite cell (stem cell), Heart muscle cells, Ordinary heart muscle cell, Nodal heart muscle cell, Purkinje fiber cell, Smooth muscle cell (various types), Myoepithelial cell of iris, Myoepithelial cell of exocrine glands can be used in the present device.

The following cells can also be used in the present device: Blood and immune system cells, such as Erythrocyte (red blood cell), Megakaryocyte (platelet precursor), Monocyte, Connective tissue macrophage (various types), Epidermal Langerhans cell, Osteoclast (in bone), Dendritic cell (in lymphoid tissues), Microglial cell (in central nervous system), Neutrophil granulocyte, Eosinophil granulocyte, Basophil granulocyte, Mast cell, Helper T cell, Suppressor T cell, Cytotoxic T cell, Natural Killer T cell, B cell, Natural killer cell, Reticulocyte, Stem cells and committed progenitors for the blood and immune system (various types). One can use these cells as single cell types or in mixtures to determine effects of the immune cells in the tissue culture system.

One can also treat the membranes with one or more Nervous system cells, Sensory transducer cells such as Auditory inner hair cell of organ of Corti, Auditory outer hair cell of organ of Corti, Basal cell of olfactory epithelium (stem cell for olfactory neurons), Cold-sensitive primary sensory neurons, Heat-sensitive primary sensory neurons, Merkel cell of epidermis (touch sensor), Olfactory receptor neuron, Pain-sensitive primary sensory neurons (various types); Photoreceptor cells of retina in eye including Photoreceptor rod cells, Photoreceptor blue-sensitive cone cell of eye, Photoreceptor green-sensitive cone cell of eye, Photoreceptor red-sensitive cone cell of eye, Proprioceptive primary sensory neurons (various types); Touch-sensitive primary sensory neurons (various types); Type I carotid body cell (blood pH sensor); Type II carotid body cell (blood pH sensor); Type I hair cell of vestibular apparatus of ear (acceleration and gravity); Type II hair cell of vestibular apparatus of ear (acceleration and gravity); and/or Type I taste bud cell.

One can further use Autonomic neuron cells such as Cholinergic neural cell (various types), Adrenergic neural cell (various types), Peptidergic neural cell (various types) in the present device. Further, sense organ and peripheral neuron supporting cells can also be used. These include, for example, Inner pillar cell of organ of Corti, Outer pillar cell of organ of Corti, Inner phalangeal cell of organ of Corti, Outer phalangeal cell of organ of Corti, Border cell of organ of Corti, Hensen cell of organ of Corti, Vestibular apparatus supporting cell, Type I taste bud supporting cell, Olfactory epithelium supporting cell, Schwann cell, Satellite cell (encapsulating peripheral nerve cell bodies) and/or Enteric glial cell. In some embodiments, one can also use central nervous system neurons and glial cells such as Astrocyte (various types), Neuron cells (large variety of types, still poorly classified), Oligodendrocyte, and Spindle neuron.

Lens cells such as Anterior lens epithelial cell and Crystallin-containing lens fiber cell can also be used in the present device. Additionally, one can use pigment cells such as melanocytes and retinal pigmented epithelial cells; and germ cells, such as Oogonium/Oocyte, Spermatid, Spermatocyte, Spermatogonium cell (stem cell for spermatocyte), and Spermatozoon.

In some embodiments one can add to the membrane nurse cells Ovarian follicle cell, Sertoli cell (in testis), Thymus epithelial cell. One can also use interstitial cells such as interstitial kidney cells.

In an embodiment, one can coat at least one side of the membrane with epithelial cells. Epithelium is a tissue composed of cells that line the cavities and surfaces of structures throughout the body. Many glands are also formed from epithelial tissue. It lies on top of connective tissue, and the two layers are separated by a basement membrane. In humans, epithelium is classified as a primary body tissue, the other ones being connective tissue, muscle tissue and nervous tissue. Epithelium is often defined by the expression of the adhesion molecule e-cadherin (as opposed to n-cadherin, which is used by neurons and cells of the connective tissue).

Functions of epithelial cells include secretion, selective absorption, protection, transcellular transport and detection of sensation and they commonly as a result present extensive apical-basolateral polarity (e.g. different membrane proteins expressed) and specialization. Examples of epithelial cells include squamous cells that have the appearance of thin, flat plates. They fit closely together in tissues; providing a smooth, low-friction surface over which fluids can move easily. The shape of the nucleus usually corresponds to the cell form and helps to identify the type of epithelium. Squamous cells tend to have horizontally flattened, elliptical nuclei because of the thin flattened form of the cell. Classically, squamous epithelia are found lining surfaces utilizing simple passive diffusion such as the alveolar epithelium in the lungs. Specialized squamous epithelia also form the lining of cavities such as the blood vessels (endothelium) and heart (mesothelium) and the major cavities found within the body.

Another example of epithelial cells is cuboidal cells. Cuboidal cells are roughly cuboidal in shape, appearing square in cross section. Each cell has a spherical nucleus in the centre. Cuboidal epithelium is commonly found in secretive or absorptive tissue: for example the (secretive) exocrine gland the pancreas and the (absorptive) lining of the kidney tubules as well as in the ducts of the glands. They also constitute the germinal epithelium which produces the egg cells in the female ovary and the sperm cells in the male testes.

Yet another type of epithelial cells are columnar epithelial cells that are elongated and column-shaped. Their nuclei are elongated and are usually located near the base of the cells. Columnar epithelium forms the lining of the stomach and intestines. Some columnar cells are specialised for sensory reception such as in the nose, ears and the taste buds of the tongue. Goblet cells (unicellular glands) are found between the columnar epithelial cells of the duodenum. They secrete mucus, which acts as a lubricant.

Still another example of the epithelial cells are pseudostratified cells. These are simple columnar epithelial cells whose nuclei appear at different heights, giving the misleading (hence "pseudo") impression that the epithelium is stratified when the cells are viewed in cross section. Pseudostratified epithelium can also possess fine hair-like extensions of their apical (luminal) membrane called cilia. In this case, the epithelium is described as "ciliated" pseudostratified epithelium. Cilia are capable of energy dependent pulsatile beating in a certain direction through interaction of cytoskeletal microtubules and connecting structural proteins and enzymes. The wafting effect produced causes mucus secreted locally by the goblet cells (to lubricate and to trap pathogens and particles) to flow in that direction (typically out of the body). Ciliated epithelium is found in the airways (nose, bronchi), but is also found in the uterus and Fallopian tubes of females, where the cilia propel the ovum to the uterus.

Epithelium lines both the outside (skin) and the inside cavities and lumen of bodies. The outermost layer of our skin is composed of dead stratified squamous, keratinised epithelial cells.

Tissues that line the inside of the mouth, the oesophagus and part of the rectum are composed of nonkeratinized stratified squamous epithelium. Other surfaces that separate body cavities from the outside environment are lined by simple squamous, columnar, or pseudostratified epithelial cells. Other epithelial cells line the insides of the lungs, the gastrointestinal tract, the reproductive and urinary tracts, and make up the exocrine and endocrine glands. The outer surface of the cornea is covered with fast-growing, easily-regenerated epithelial cells. Endothelium (the inner lining of blood vessels, the heart, and lymphatic vessels) is a specialized form of epithelium. Another type, mesothelium, forms the walls of the pericardium, pleurae, and peritoneum.

Accordingly, one can recreate any of these tissues in the cell culture device as described by plating applicable cell types on the porous membranes and applying applicable vacuum to provide physiological or artificial mechanical force on the cells to mimic physiological forces, such as tension on skin or mechanical strain on lung. In an embodiment, one side of the membrane is coated with epithelial cells and the other side is coated with endothelial cells.

The endothelium is the thin layer of cells that line the interior surface of blood vessels, forming an interface between circulating blood in the lumen and the rest of the vessel wall. Endothelial cells line the entire circulatory system, from the heart to the smallest capillary. These cells reduce turbulence of the flow of blood allowing the fluid to be pumped farther. Endothelial tissue is a specialized type of epithelium tissue (one of the four types of biological tissue in animals). More specifically, it is simple squamous epithelium.

The foundational model of anatomy makes a distinction between endothelial cells and epithelial cells on the basis of which tissues they develop from and states that the presence of vimentin rather than keratin filaments separate these from epithelial cells. Endothelium of the interior surfaces of the heart chambers are called endocardium. Both blood and lymphatic capillaries are composed of a single layer of endothelial cells called a monolayer. Endothelial cells are involved in many aspects of vascular biology, including: vasoconstriction and vasodilation, and hence the control of blood pressure; blood clotting (thrombosis & fibrinolysis); atherosclerosis; formation of new blood vessels (angiogenesis); inflammation and barrier function—the endothelium acts as a selective barrier between the vessel lumen and surrounding tissue, controlling the passage of materials and the transit of white blood cells into and out of the bloodstream. Excessive or prolonged increases in permeability of the endothelial monolayer, as in cases of chronic inflammation, may lead to tissue oedema/swelling. In some organs, there are highly differentiated endothelial cells to perform specialized 'filtering' functions. Examples of such unique endothelial structures include the renal glomerulus and the blood-brain barrier.

In an embodiment, the membrane side that contains culturedendothelial cells can be exposed to various test substances and also white blood cells or specific immune system cells to study effects of the test agents on the function of the immune system cells at the tissue level.

Details on how the tissue interface device 200 is formed will now be discussed in accordance with an embodiment. The fabrication of the PDMS membrane preferably involves parallel processing of multiple parts which are assembled in stages. FIG. 4A illustrates a perspective view of a master 600 in accordance with an embodiment which is ultimately used to produce the porous membrane 208. As shown in FIG. 4A, the master 600 is preferably formed by patterning a photoresist to the desired shape and size on a silicon substrate.

It should be noted that the posts 602 may be designed in any desired array depending on the intended design of the membrane 208. For example, the posts 602 may be arranged in a circular pattern to correspondingly form a circular patterned set of pores in the membrane 208. It should be noted that the posts 602 may have any other cross sectional shape other than pentagonal to make the corresponding pores in the membrane, as discussed above. It should also be noted that the master 600 may contain different height ridges to create non planar membranes.

Thereafter, as shown in FIG. 4B, the master 600 is preferably spin-coated with PDMS to form a spin coated layer 604. Thereafter, the spin-coated layer 604 is cured for a set time and temperature (e.g. 110° C. at 15 minutes) and peeled off the master 600 to produce a thin PDMS membrane 604 having the array of pentagonal through-holes 606, as shown in FIG. 4C. The example shown depicts fabrication of a 10 µm-thick PDMS membrane, although other thickness values are contemplated.

Although other materials may be used, PDMS has useful properties in biology in that it is a moderately stiff elastomer (1 MPa) which is non-toxic and is optically transparent to 300 nm. PDMS is intrinsically very hydrophobic, but can be converted to hydrophilic form by treatment with plasma. The membrane 604 may be engineered for a variety of purposes, some discussed above. For example, the pores 606 on the membrane 604 may be coated or filled with ECM molecules or gels, such as MATRIGEL, laminin, collagen, fibronectin, fibrin, elastin, etc., which are known to those skilled in the art. The tissue-tissue interface may be coated by culturing different types of cells on each side of the membrane 604, as shown in FIG. 4D. In particular, as shown in FIG. 4D, one type of cells 608 are coated on one side of the membrane 604 whereas another type of cells 610 are coated on the opposing side of the membrane 604.

FIGS. 5A and 5B illustrate the process how the first outer body portion 202, a second outer body portion 204 are formed in accordance with an embodiment. The first and second outer body portions 202, 204 are preferably formed using soft lithography techniques, although other techniques well known in the art are contemplated. In an embodiment, a photoresist (not shown) is formed on a substrate in which the photoresist has positive relief features which minor the desired branching configuration in the first outer body portion. Similarly, a second photoresist (not shown) is formed on another substrate in which the second photoresist has corresponding positive relief features which mirror the branching configuration in the second outer body portion 204. The microchannels along with the communicating ports and port apertures are preferably generated by preferably casting PDMS or other appropriate material onto each master. Once the first and second outer body portions 202, 204 are formed, through-holes which serve as the port apertures are made through the PDMS slab preferably using an aperture forming mechanism or stamp.

As shown in FIG. 5C, the already formed PDMS membrane 208 is then sandwiched between the first outer body portion 202 and the second outer body portion 204, whereby the microchannel walls 234, 244 as well as the outside walls 238, 248 are aligned using appropriate manufacturing equipment and techniques. Thereafter, the microchannel walls 234, 244 and outside walls are preferably bonded to the membrane 208 using an appropriate adhesive or epoxy. Additionally, the remaining portions of the outer body portions 202, 204 are permanently bonded to one another using an appropriate adhesive or epoxy to form the overall device.

Subsequently, as shown in FIG. 5D, a PDMS etching solution is introduced into the operating channels to etch away the PDMS membrane segments in the operating channels. This results in resulting in the generation of the two side operating channels 252 being free from the membrane, although the membrane is maintained in the central microchannel, as shown in FIG. 5E. The above is preferably formed using soft lithography techniques, the details of which are described in "Soft Lithography in Biology and Biochemistry," by Whitesides, et al., published Annual Review, Biomed Engineering, 3.335-3.373 (2001), as well as "An Ultra-Thin PDMS Membrane As A Bio/Micro-Nano Interface: Fabrication And Characterization", by Thangawng et al., Biomed Microdevices, vol. 9, num. 4, 2007, p. 587-95, both of which are hereby incorporated by reference.

Figure 6:
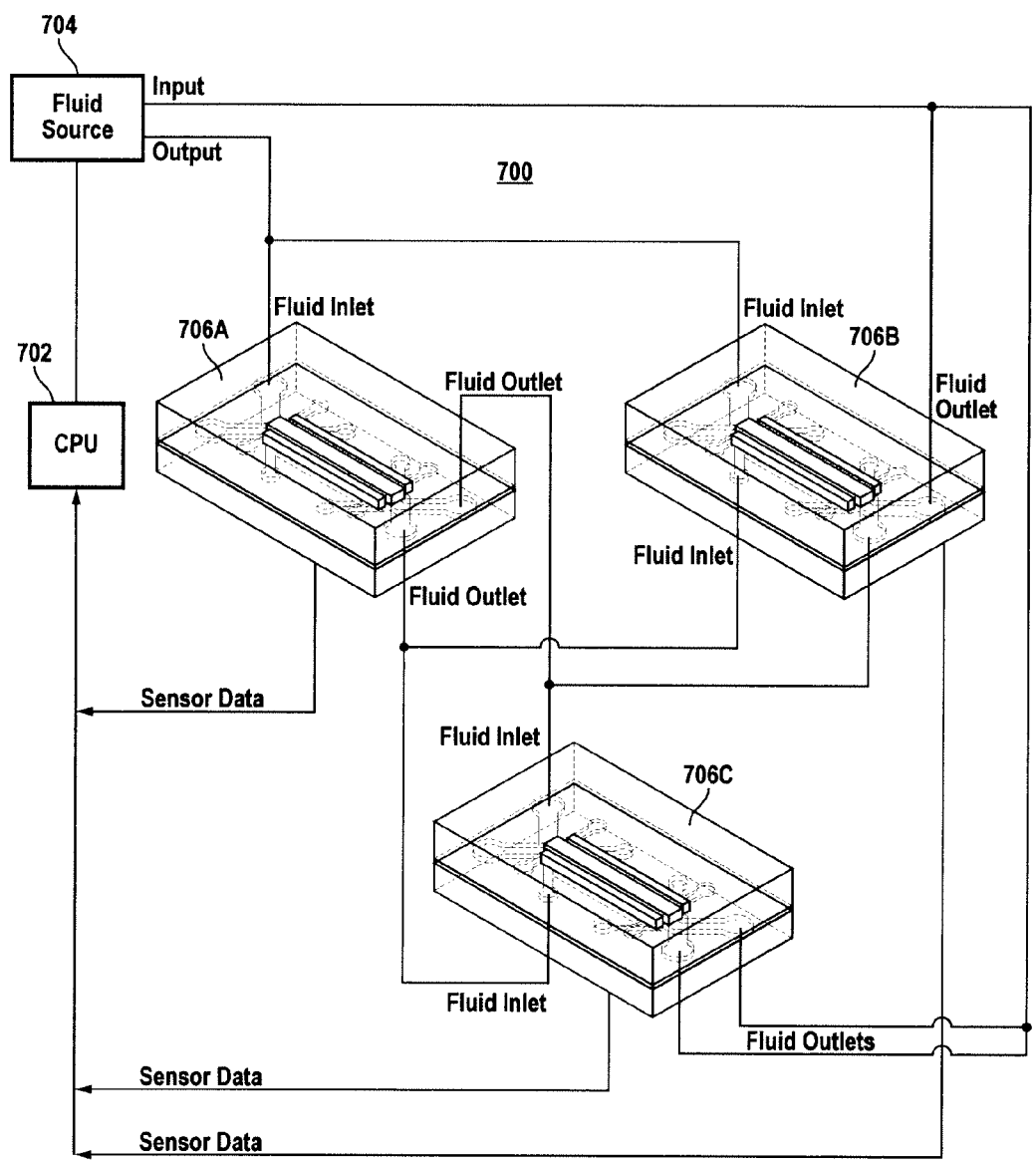
FIG. 6 illustrates a system diagram employing an organ mimic device with multiple channels in accordance with an embodiment.

FIG. 6 illustrates a schematic of a system having multiple tissue interface devices in accordance with an embodiment. In particular, as shown in FIG. 6, the system 700 includes one or more CPUs 702 coupled to one or more fluid sources 704 and pressure sources (not shown), whereby the preceding are coupled to three shown tissue interface devices 706A, 706B, and 706C. It should be noted that although three devices 706 are shown in this embodiment, fewer or greater than three devices 706 are contemplated. In the system 700, two of the three devices (i.e. 706A and 706B) are connected in parallel with respect to the fluid source 704 and devices 706A and 706C are connected in serial fashion with respect to the fluid source 704. It should be noted that the shown configuration is only one example and any other types of connection patterns may be utilized depending on the application.

In the example shown, fluid from the fluid source 704 is provided directly to the fluid inlets of devices 706A and 706B. As the fluid passes through device 706A, it is output directly into the fluid inlet port of devices 706B and 706C. Additionally, the fluid outlet from device 706B is combined with the output from device 706A into device 706C. With multiple devices operating, it is possible to monitor, using sensor data, how the cells in the fluid or membrane behave after the fluid has been passed through another controlled environment. This system thus allows multiple independent "stages" to be set up, where cell behavior in each stage may be monitored under simulated physiological conditions and controlled using the devices 706. One or more devices are connected serially may provide use in studying chemical communication between cells. For example, one cell type may secrete protein A in response to being exposed to a particular fluid, whereby the fluid, containing the secreted protein A, exits one device and then is exposed to another cell type specifically patterned in another device, whereby the interaction of the fluid with protein A with the other cells in the other device can be monitored (e.g. paracrine signaling). For the parallel configuration, one or more devices connected in parallel may be advantageous in increasing the efficiency of analyzing cell behavior across multiple devices at once instead of analyzing the cell behavior through individual devices separately.

Figure 7A:
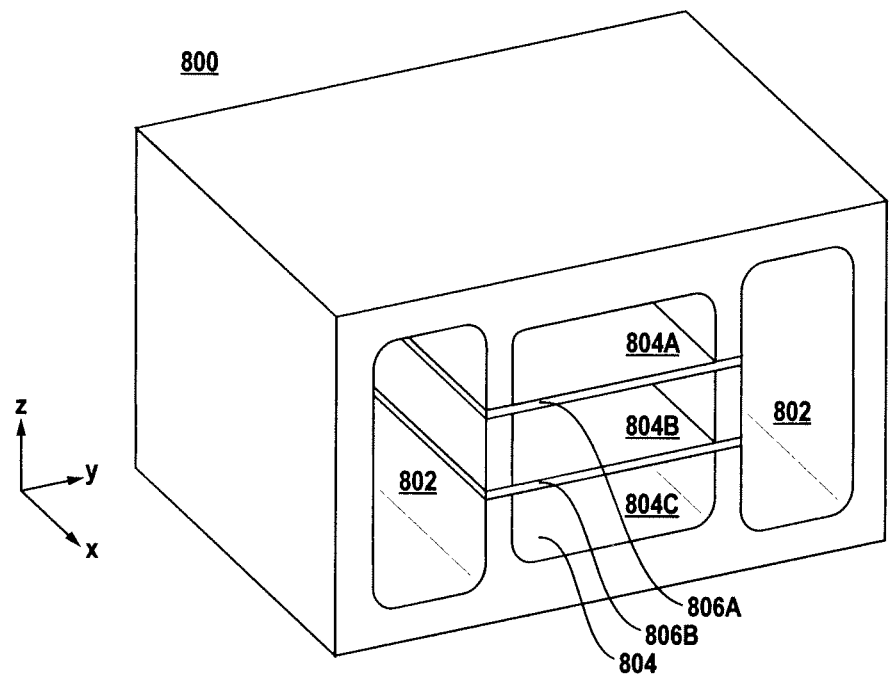
FIGS. 7A-7B illustrate perspective views of the organ mimic device in accordance with an embodiment.

FIG. 7A illustrates a perspective view of an organ mimic device in accordance with an embodiment that contains three parallel microchannels separated by two porous membranes. As shown in FIG. 7A, the organ mimic device 800 includes operating microchannels 802 and an overall central microchannel 804 positioned between the operating microchannels 802. The overall central microchannel 804 includes multiple membranes 806A, 806B positioned along respective parallel x-y planes which separate the microchannel 804 into three distinct central microchannels 804A, 804B and 804C. The membranes 806A and 806B may be porous, elastic, or a combination thereof. Positive and/or negative pressurized media may be applied via operating channels 802 to create a pressure differential to thereby cause the membranes 806A, 806B to expand and contract along their respective planes in parallel.

Figure 7B:
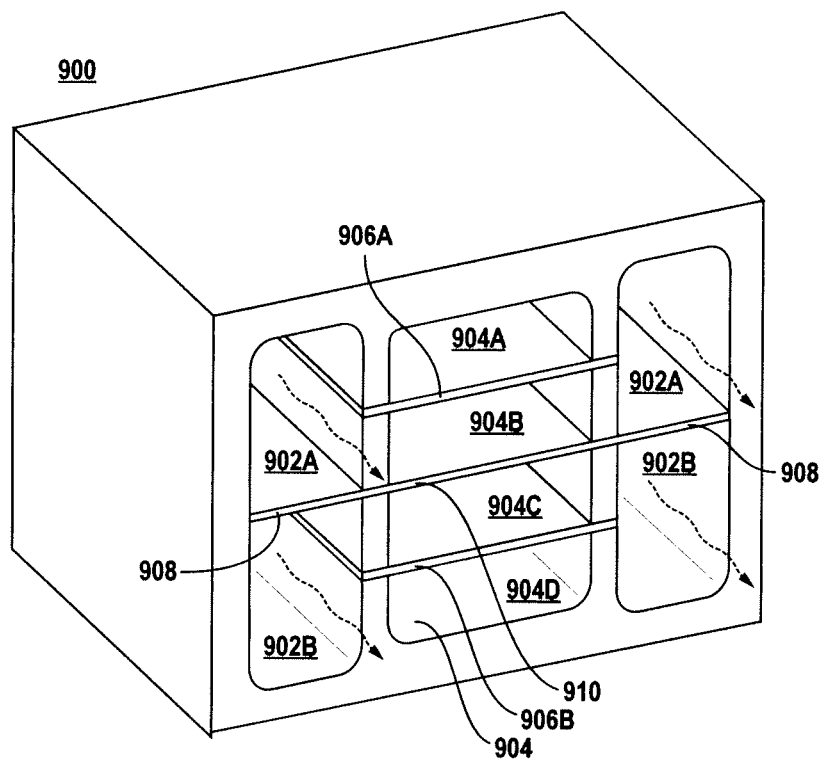

FIG. 7B illustrates a perspective view of an organ mimic device in accordance with an embodiment. As shown in FIG. 7B, the tissue interface device 900 includes operating microchannels 902A, 902B and a central microchannel 904 positioned between the microchannels 902. The central microchannel 904 includes multiple membranes 906A, 906B positioned along respective parallel x-y planes. Additionally, a wall 910 separates the central microchannel into two distinct central microchannels, having respective sections, whereby the wall 910 along with membranes 904A and 904B define microchannels 904A, 904B, 904C, and 904D. The membranes 906A and 906B at least partially porous, elastic or a combination thereof.

The device in FIG. 7B differs from that in FIG. 7A in that the operating microchannels 902A and 902B are separated by a wall 908, whereby separate pressures applied to the microchannels 902A and 902B cause their respective membranes 904A and 904B to expand or contract. In particular, a positive and/or negative pressure may be applied via operating microchannels 902A to cause the membrane 906A to expand and contract along its plane while a different positive and/or negative pressure is applied via operating microchannels 902B to cause the membrane 906B to expand and contract along its plane at a different frequency and/or magnitude. Of course, one set of operating microchannels may experience the pressure while the other set does not experience a pressure, thereby only causing one membrane to actuate. It should be noted that although two membranes are shown in the devices 800 and 900, more than two membranes are contemplated and can be configured in the devices.

In an example, shown in FIG. 7C, the device containing three channels described in FIG. 7A has two membranes 806A and 806B which are coated to determine cell behavior of a vascularized tumor. In particular, membrane 806A is coated with a lymphatic endothelium on its upper surface 805A and with stromal cells on its lower surface, and stromal cells are also coated on the upper surface of the second porous membrane 805B and a vascular endothelium on its bottom surface 805C. Tumor cells are placed in the central microchannel surrounded on top and bottom by layers of stromal cells on the surfaces of the upper and lower membranes in section 804B. Fluid such as cell culture medium or blood enters the vascular channel in section 804C. Fluid such as cell culture medium or lymph enters the lymphatic channel in section 804A. This configuration of the device 800 allows researchers to mimic and study tumor growth and invasion into blood and lymphatic vessels during cancer metastasis. In the example, one or more of the membranes 806A, 806B may expand/contract in response to pressure through the operating microchannels. Additionally or alternatively, the membranes may not actuate, but may be porous or have grooves to allow cells to pass through the membranes.

The unique capabilities of the present device have been monitored in experiments that address acute toxicity and extrapulmonary translocation of engineered nanomaterials induced by physiological mechanical forces. The device has been used to model pulmonary inflammation in which it can precisely recreate and directly visualize the complex interplay of pulmonary tissues with cytokines and blood-borne immune cells that transmigrate across the alveolar-capillary barrier. Using this model, the device reveals significant inflammatory responses of the mimicked lung to nanomaterials. Finally, the device is used to simulate pulmonary infection with bacteria and its clearance by neutrophil recruitment and phagocytosis.

The device has been used in experiments which have led to the discovery that physiological mechanical forces can induce or exacerbate toxicity of engineered nanomaterials in the lung and may facilitate their translocation into the systemic circulation. Furthermore, in vitro models that simulate lung inflammation have been developed that enable direct observation of the adhesion of circulating blood-borne immune cells to inflamed endothelia and their transmigration across the alveolar-capillary barrier. Based on this model, significant proinflammatory activities of engineered nanoparticles have been revealed. Based on this evidence, a model of pulmonary infection can be established and re-creation may be done of the innate immune response of the lung to bacteria mediated by neutrophil infiltration into the alveoli and bacterial phagocytosis.

The present device was utilized in several experiments, whereby the device was used to mimic the living lung. The observations and findings with the present device are described hereafter. During normal inspiration of a real lung, the thoracic cavity enlarges due to the contraction of the diaphragm and expansion of the rib-cage and, as a result, the intrapleural pressure outside the alveoli decreases. The increased pressure difference across the alveolar wall causes the alveoli to expand and forces air into the lungs, resulting in stretching of the alveolar epithelium and endothelium in the surrounding capillaries. Alveolar epithelial cells are co-cultured with pulmonary microvascular endothelial cells on a thin porous membrane to produce two opposing tissue layers that mimic the interface between the alveolar epithelium and pulmonary endothelium. The compartmentalized microchannel configuration makes it readily possible to manipulate fluidic environment of the epithelium and endothelium independently, and to apply physiological mechanical strain.

In the experiment, co-culture of alveolar epithelial cells and primary pulmonary microvascular endothelial cells of human origin was developed over two weeks without loss of viability. The microfluidic culture resulted in the production of tight alveolar-capillary barriers with structural integrity as evidenced by typical junctional complexes present in both epithelial and endothelial layers. The microfluidic device was integrated with computer-controlled vacuum to enable cyclic membrane/cell stretching at varying frequencies and levels of strain in a programmable manner. It was observed that applied vacuum generated unidirectional tension which is uniform across the wide central microchannel. Concurrently, it was discovered that this tension was perceived by adherent cells and caused them to stretch and increase their projected surface area. Also effective application of mechanical strain to cells was confirmed by showing stretch-induced alignment and transient calcium responses of endothelial cells.

Based on the unique capabilities afforded by on-chip production of pulmonary tissues and faithful recapitulation of their native microenvironment, the device was used to assess the potential adverse effects of nanomaterials. Despite the widespread use of engineered nanomaterials, much remains to be learned about their risks to health and environment. Existing toxicology methods rely on oversimplified in vitro models or lengthy, expensive animal testing that often poses challenges to mechanistic studies at the cellular level. To bridge the gap between cell culture studies and animal models, the device was used to permit a more realistic, accurate evaluation of nanomaterial toxicity in a tightly controlled biomimetic microenvironment.

Figure 8:
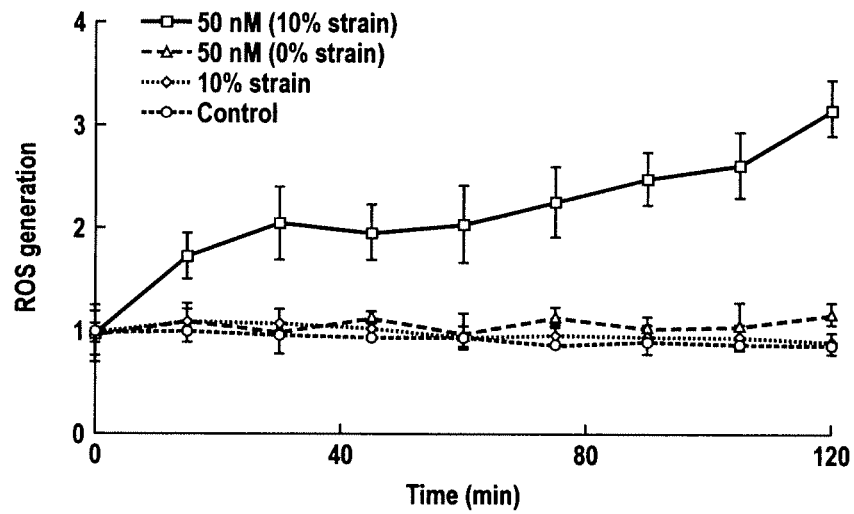
FIGS. 8 and 9 illustrate ROS generation over time in accordance with an experiment conducting with the present device.

In the experiment, the alveolar epithelial tissues prepared in the device were exposed to various nanomaterials and oxidative stress was examined by measuring intracellular production of reactive oxygen species (ROS) using microfluorimetry. Through the testing of colloidal silica nanoparticles and quantum dots, it was discovered that physiological mechanical strain can dramatically increase nanoparticle-generated oxidative stress and induce early toxic responses in the pulmonary epithelium. For example, when the cells were exposed to 12 nm silica nanoparticles in combination with a cyclic stretch of 10% strain at 0.2 Hz which simulates normal respiration, ROS production increased by more than five times after two hours, whereas nanoparticles or mechanical strain alone did not cause any measurable responses over the duration of the experiments (see FIG. 8). The response of cells treated with carboxylated quantum dots showed similar trends (see FIG. 9). It was noted that similar levels of ROS increase were achieved after 24 hour-long exposures to silica nanoparticles alone, as shown in FIG. 9.

Figure 9:
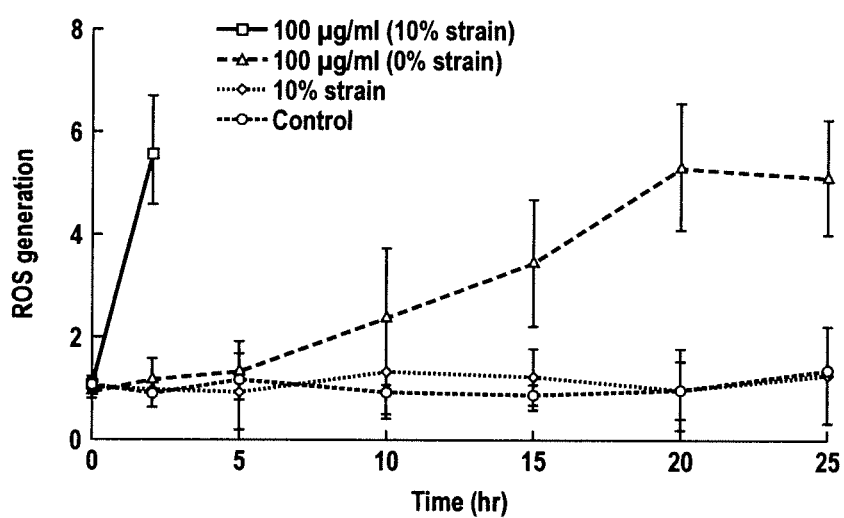

It was also found that cyclic strain alone did not have any significant impact regardless of its duration, as shown in FIG. 9. Taken together, these observations suggest that physiological forces act in synergy with nanoparticles to exert early toxic effects or aggravate nanoparticle toxicity in the lung. This stretch-induced ROS response to nanomaterials depended on the level of strain and induced apoptosis of the epithelial cells as detected by caspase activity. When treated with a clinically used free radical scavenger, N-acetylcysteine (NAC) during nanoparticle exposure, the cells were completely rescued from oxidative stress presumably due to the antioxidant activity of NAC leading to increased intracellular glutathione. It was also observed that oxidative stress generated by the combined effect of nanomaterials and strain varied significantly with the type of nanomaterials. For example, exposures to 50 nm superparamagnetic iron nanoparticles under the same conditions only resulted in a transient increase in oxidative stress. This unique ROS response was not observed in the testing of other nanomaterials including single walled carbon nanotubes, gold nanoparticles, polystyrene nanoparticles, and quantum dots coated with polyethylene glycol, as shown below in Table 1.

TABLE 1

| Nanomaterials | Surface coating | Size | ROS response (0% strain) | ROS response (10% strain) |
|---|---|---|---|---|
| Polystyrene nanoparticles | Carboxyl groups | 500 nm | No | No |
|  | Carboxyl groups | 200 nm | No | No |
|  | Amine groups | 200 nm | No | No |
|  | Carboxyl groups | 100 nm | No | No |
|  | Carboxyl groups | 20 nm | No | No |
| Quantum dots | Carboxyl groups | 16 nm | No | Yes |
|  | polyethylene glycol | 13 nm | No | No |
| Silica nanoparticles | N/A | 12 nm | No | Yes |
| Magnetic iron nanoparticles | Carboxyl groups | 50 nm | No | Yes |
| Gold nanoparticles | N/A | 3 nm | No | No |

To understand the influence of physiological forces on tissue-nanomaterial interactions, confocal microscopy was used to analyze internalization of 100 nm fluorescent nanoparticles into the epithelial cells after 1 hour of exposure. However, the number of particles or their aggregates detected in intracellular compartments was much greater in the presence of mechanical strain, and over 80% of the cells were found to have taken up the nanoparticles, whereas the extent of nanoparticle uptake was considerably smaller in the absence of strain. These results indicate that physiological mechanical forces may facilitate cellular uptake of nanomaterials, allowing them to interact with subcellular components and thereby rendering them potentially more harmful.

Moreover, the device provides an opportunity to investigate extrapulmonary translocation of nanomaterials from the alveolar space to the microvasculature. Increasing in vivo evidence suggests that nanomaterials in the alveoli have the capacity to cross the alveolar-capillary barrier and enter the pulmonary circulation, potentially impacting other organs. To investigate this situation, 20 nm fluorescent nanoparticles were introduced on the epithelial side and nanoparticle translocation was monitored by counting the number of particles carried out of the lower vascular channel by continuous fluid flow. This model revealed a marked increase in the rate of nanoparticle migration into the vascular compartment under physiological conditions with 10% cyclic strain, as compared to transport across a relaxed, static tissue barrier. These findings provide in vitro evidence that the inherent mechanical activity of the living lung may allow nanomaterials to translocate from the alveolar space into the bloodstream. The data from the experiment also supports the systematic distribution and accumulation of inhaled nanomaterials observed in animal studies and may potentially contribute to delineating the mechanism of this process, as well as providing a surrogate model system for studying this response.

To further demonstrate the device's capabilities to reconstitute the integrated organ-level responses in the lung, a more sophisticated model was developed that incorporated circulating blood-borne immune cells and reproduced the key steps of lung inflammation. Generally, inflammatory responses in the lung involve a highly coordinated multistep cascade of epithelial production and release of early response cytokines, activation of vascular endothelium through upregulation of leukocyte adhesion molecules and subsequent leukocyte infiltration from the pulmonary microcirculation into the alveolar space. To simulate this process, the apical surface of the alveolar epithelium was first stimulated with tumor necrosis factor-$\alpha$ (TNF-$\alpha$), which is a potent pro-inflammatory mediator, and endothelial activation was examined by measuring the expression of intercellular adhesion molecule-1 (ICAM-1). In response to TNF-$\alpha$ stimulation of the alveolar tissue for 5 hours, the endothelial cells on the opposite side of the membrane dramatically increased their surface expression of ICAM-1. Furthermore, the activated endothelium supported capture and firm adhesion of human neutrophils flowing in the vascular microchannel, which did not adhere in the absence of cytokine exposure. Treatment of the epithelial cells with low doses of TNF-$\alpha$ resulted in weak activation of the endothelium, which caused captured neutrophils to roll continuously in the direction of flow without being arrested. Direct microscopic visualization revealed that adherent neutrophils became flattened and crawled from a site of firm adhesion to distant locations where they extravasated through the endothelium and transmigrated across the alveolar-capillary barrier through the membrane pores over the period of several minutes. The transmigrated neutrophils then emigrated onto the apical surface of the alveolar epithelium preferentially through paracellular junctions and were retained on the epithelial layer in spite of fluid flow and cyclic stretching. These sequential events successfully replicate the entire process of neutrophil recruitment from the microvasculature to the alveolar compartment, which is a hallmark of lung inflammation.

Using the device, proinflammatory effects of colloidal silica nanoparticles on the lung were investigated. Upon the alveolar epithelial cells being exposed to 12 nm silica nanoparticles for 5 hours, the microvascular endothelium became activated and exhibited high levels of ICAM-1 expression. It was noted that application of 10% cyclic strain along with nanoparticles synergistically upregulated endothelial expression of ICAM-1. Human neutrophils circulating in the vascular channel were seen to firmly adhere to the inflamed endothelium, to transmigrate across the tissue barrier, and to accumulate on the epithelial surface. These observations evidence significant proinflammatory activities of these silica nanoparticles, which may become more pronounced due to physiological forces that provoke acute inflammation in the lung.

In an experiment, the present device was configured to mimic the innate immune response to pulmonary infection of bacterial origin. To imitate the lung afflicted with bacterial infection, alveolar epithelial cells were apically stimulated with *Escherichia coli* (*E. coli*) constitutively expressing green fluorescent protein (GFP) for 5 hours. When human neutrophils were subsequently allowed to flow in the vascular microchannel, they attached to the endothelial cells and underwent diapedesis across the tissue layers, indicating that bacterial stimulation of the epithelium gave rise to endothelial activation. Upon reaching the epithelial surface, the neutrophils showed directional movement towards GFP-labeled bacteria and engulfed them as illustrated by detection of phagocytosed bacteria with fluorescently labeled moving neutrophils. It was also observed that neutrophils are capable of ingesting more than one bacterium over short periods of time and that their phagocytic activity continued until a majority of the bacteria were cleared from the observation area. These results clearly demonstrate the ability of this model to recreate the complete process of the integrated immune response to microbial infection within a 3D physiological organ context in vitro.

While embodiments and applications have been shown and described, it would be apparent to those skilled in the art having the benefit of this disclosure that many more modifications than mentioned above are possible without departing from the inventive concepts disclosed herein. The embodiment(s), therefore, are not to be restricted except in the spirit of the appended claims.

The present inventive subject matter can be defined in any of the following alphabetized paragraphs:

[A] An organomimetic device comprising:
a body having a central microchannel therein; and
an at least partially porous membrane positioned within the central microchannel and along a plane, the membrane configured to separate the central microchannel to form a first central microchannel and a second central microchannel, wherein a first fluid is applied through the first central microchannel and a second fluid is applied through the second central microchannel, the membrane coated with at least one attachment molecule that supports adhesion of a plurality of living cells.

[B] The device of [A] wherein the porous membrane is at least partially flexible, the device further comprising:
a first chamber wall of the body positioned adjacent to the first and second central microchannels, wherein the membrane is mounted to the first chamber wall; and
a first operating channel adjacent to the first and second central microchannels on an opposing side of the first chamber wall, wherein a pressure differential applied between the first operating channel and the central microchannels causes the first chamber wall to flex in a first desired direction to expand or contract along the plane within the first and second central microchannels.

[C] The device of [A] or [B] further comprising:

a second chamber wall of the body positioned adjacent to the first and second central microchannels, wherein an opposing end of the membrane is mounted to the second chamber wall; and a second operating channel positioned adjacent to the central microchannel on an opposing side of the second chamber wall, wherein the pressure differential between to the second operating channel and the central microchannels causes the second chamber wall to flex in a second desired direction to expand or contract along the plane within the first and second central microchannels.

[D] The device of any or all of the above paragraphs wherein at least one pore aperture in the membrane is between 0.5 and 20 microns along a width dimension.

[E] The device of any or all of the above paragraphs wherein the membrane further comprises a first membrane and a second membrane positioned within the central microchannel, wherein the second membrane is oriented parallel to the first membrane to form a third central microchannel therebetween.

[F] The device of any or all of the above paragraphs wherein the membrane comprises PDMS,

[G] The device of any or all of the above paragraphs wherein the membrane is coated with one or more cell layers, wherein the one or more cell layers are applied to a surface of the membrane.

[H] The device of any or all of the above paragraphs wherein one or both sides of the membrane are coated with one or more cell layers, wherein the one or more cell layers comprise cells selected from the group consisting of metazoan, mammalian, and human cells.

[I] The device of any or all of the above paragraphs, wherein the cells are selected from the group consisting of epithelial, endothelial, mesenchymal, muscle, immune, neural, and hemapoietic cells.

[J] The device of any or all of the above paragraphs wherein one side of the membrane is coated with epithelial cells and the other side of the membrane is coated with endothelial cells.

[K] The device of any or all of the above paragraphs wherein the body of the device and the membrane are made of a biocompatible or biodegradable material.

[L] The device of any or all of the above paragraphs wherein the device is further implanted to a living organism.

[M] The device of any or all of the above paragraphs wherein the living organism is a human.

[N] The device of any or all of the above paragraphs wherein the membrane is coated with the one or more cell layers in vitro.

[O] The device of any or all of the above paragraphs, wherein the at least one membrane is coated with the one or more cell layers in vivo.

[P] The device of any or all of the above paragraphs, wherein the membrane is coated with a biocompatible agent which facilitates attachment of the at least one cell layer onto the membrane.

[Q] The device of any or all of the above paragraphs wherein the biocompatible agent is extracellular matrix comprising collagen, fibronectin and/or laminin.

[R] The device of any or all of the above paragraphs wherein the biocompatible material is selected from the group consisting of collagen, laminin, proteoglycan, vitronectin, fibronectin, poly-D-lysine and polysaccharide.

[S] The device of any or all of the above paragraphs wherein the first fluid contains white blood cells.

[T] A method comprising:

selecting a organomimetic device having a body, the body including an at least partially porous membrane positioned along a plane within a central microchannel to partition the central microchannel into a first central microchannel and a second central microchannel, the membrane coated with at least one attachment molecule that supports adhesion of a plurality of living cells;

applying a first fluid through the first central microchannel;

applying a second fluid through the second central microchannel; and monitoring behavior of cells with respect to the membrane between the first and second central microchannels.

[U] The method of any or all of the above paragraphs wherein the membrane is at least partially elastic and the body includes at least one operating channel positioned adjacent to the first and second central microchannels, the method further comprising:

adjusting a pressure differential between the central microchannels and the at least one operating channels, wherein the membrane stretches along the plane in response to the pressure differential.

[V] The method of any or all of the above paragraphs wherein the adjusting of the pressure differential further comprises:

increasing the pressure differential such that one or more sides of the membrane move in desired directions along the plane; and decreasing the pressure differential such that the one or more sides of the membrane move in an opposite direction along the plane.

[W] The method of any or all of the above paragraphs wherein at least one pore aperture in the membrane is between 0.5 and 20 microns along a width dimension.

[X] The method of any or all of the above paragraphs further comprising treating the membrane with one or more cell layers, wherein the one or more cell layers are applied to a surface of the membrane.

[Y] The method of any or all of the above paragraphs further comprising applying one or more cell layers onto one or both sides of the membrane, wherein the one or more cell layers comprise cells selected from the group consisting of metazoan, mammalian, and human cells.

[Z] The method of any or all of the above paragraphs wherein the cells are selected from the group consisting of epithelial, endothelial, mesenchymal, muscle, immune, neural, and hemapoietic cells.

[AA] The method of any or all of the above paragraphs wherein one side of the membrane is coated with epithelial cells and the other side of the membrane is coated with endothelial cells.

[BB] The method of any or all of the above paragraphs wherein the body of the device and the membrane are made of a biocompatible or biodegradable material.

[CC] The method of any or all of the above paragraphs wherein the device is further implanted to a living organism.

[DD] The method of any or all of the above paragraphs wherein the living organism is a human.

[EE] The method of any or all of the above paragraphs wherein the membrane is coated with the one or more cell layers in vitro.

[FF] The method of any or all of the above paragraphs wherein the at least one membrane is coated with the one or more cell layers in vivo.

[GG] The method of any or all of the above paragraphs wherein the membrane is coated with a biocompatible agent which facilitates attachment of the at least one cell layer onto the membrane.

[HH] The method of any or all of the above paragraphs wherein the biocompatible agent is extracellular matrix comprising collagen, fibronectin and/or laminin.

[II] The method of any or all of the above paragraphs wherein the biocompatible material is selected from the group consisting of collagen, laminin, proteoglycan, vitronectin, fibronectin, poly-D-lysine and polysaccharide.

[JJ] The method of any or all of the above paragraphs wherein the first fluid contains white blood cells.

[KK] A method for determining an effect of at least one agent in a tissue system with physiological or pathological mechanical force, the method comprising:

selecting a device having a body, the body including an at least partially porous membrane positioned along a plane within a central microchannel to partition the central microchannel into a first central microchannel and a second central microchannel;

contacting the membrane with at least one layer of cells on a first side of the membrane and at least one layer of cells on a second side of the porous membrane thereby forming a tissue structure comprising at least two different types of cells;

contacting the tissue structure comprising at least two different types of cells with the at least one agent in an applicable cell culture medium;

applying uniform or non-uniform force on the cells for a time period; and measuring a response of the cells in the tissue structure comprising at least two different types of cells to determine the effect of the at least one agent on the cells.

[LL] The method of any or all of the above paragraphs wherein the applicable cell culture medium is supplemented with white blood cells.

[MM] The method of any or all of the above paragraphs wherein the uniform or non-uniform force is applied using vacuum.

[NN] The method of any or all of the above paragraphs wherein the tissue structure comprising at least two different types of cells comprises alveolar epithelial cells on the first side of the porous membrane and pulmonary microvascular cells on the second side of the porous membrane.

[OO] The method of any or all of the above paragraphs wherein the agent is selected from the group consisting of nanoparticles, environmental toxins or pollutant, cigarette smoke, chemicals or particles used in cosmetic products, drugs or drug candidates, aerosols, naturally occurring particles including pollen, chemical weapons, single or double-stranded nucleic acids, viruses, bacteria and unicellular organisms.

[PP] The method of any or all of the above paragraphs wherein the measuring the response is performed by measuring expression of reactive oxygen species.

[QQ] The method of any or all of the above paragraphs wherein the measuring the response is performed using tissue staining.

[RR] The method of any or all of the above paragraphs further comprising prior to measuring the effect of the agent, taking a biopsy of the membrane comprising tissue structure comprising at least two different types of cells, wherein the biopsy is stained.

[SS] The method of any or all of the above paragraphs wherein the measuring the response is performed from a sample of the cell culture medium in contact wherein the measuring the response is performed from a sample of the cell culture medium in contact with the first or the second or both sides of the membrane form tissue structure comprising at least two different types of cells. with the first or the second or both sides of the membrane comprising tissue structure comprising at least two different types of cells.

[TT] The method of any or all of the above paragraphs further comprising comparing the effect of the agent to another agent or a control without the agent in a similar parallel device system.

[UU] The method of any or all of the above paragraphs further comprising a step of contacting the membrane with at least two agents, wherein the first agent is contacted first to cause an effect on the tissue structure comprising at least two different types of cells and the at least second agent in contacted after a time period to test the effect of the second agent on the tissue structure comprising at least two different types of cells affected with the first agent.

[VV] An organomimetic device comprising: a body having a central microchannel; and a plurality of membranes positioned along parallel planes in the central microchannel, wherein at least one of the plurality of membranes is at least partially porous, the plurality of membranes configured to partition the central microchannel into a plurality of central microchannels.

What is claimed is:

1. An organomimetic device comprising:
   a body having a central microchannel therein; and
   an at least partially porous membrane positioned within the central microchannel and along a plane, the membrane configured to separate the central microchannel to form a first central microchannel and a second central microchannel, wherein a first fluid is applied through the first central microchannel and a second fluid is applied through the second central microchannel, the membrane coated with at least one attachment molecule that supports adhesion of a plurality of living cells wherein the porous membrane is at least partially flexible, the device further comprising:
   a first operating channel separated the first and second central microchannels by a first microchannel wall, wherein the membrane is fixed to the first chamber microchannel wall; and wherein applying a pressure to the first operating channel causes the membrane to flex in a first desired direction to expand or contract along the plane within the first and second central microchannels.

2. The device of claim 1, further comprising:
   a second operating channel separated from the first and second central microchannels by a second microchannel wall, wherein an opposing end of the membrane is fixed to the second
   microchannel wall, when a pressure is applied to the second operating channel, it causes the membrane to flex in a second desired direction to expand or contract along the plane within the first and second central microchannels.

3. The device of claim 1, wherein at least one pore aperture in the membrane is between 0.5 and 20 microns along a width dimension.

4. The device of claim 1, wherein the membrane further comprises a first membrane and a second membrane positioned within the central microchannel, wherein the second membrane is oriented parallel to the first membrane to form a third central microchannel therebetween.

5. The device of claim 1, wherein the membrane comprises PDMS.

6. The device of claim 1, wherein the membrane is coated with one or more cell layers, wherein the one or more cell layers are applied to a surface of the membrane.

7. The device of claim 1, wherein one or both sides of the membrane are treated with one or more cell layers, wherein the one or more cell layers comprise cells selected from the group consisting of metazoan, mammalian, and human cells.

8. The device of claim 7, wherein the cells are selected from the group consisting of epithelial, endothelial, mesenchymal, muscle, immune, neural, and hemapoietic cells.

9. The device of claim 7, wherein one side of the membrane is treated with epithelial cells and the other side of the membrane is treated with endothelial cells.

10. The device of claim 7, wherein the body of the device and the membrane are made of a biocompatible or biodegradable material.

11. The device of claim 7, wherein the membrane is coated with a biocompatible agent which facilitates attachment of the at least one cell layer onto the membrane.

12. The device of claim 11, wherein the biocompatible agent is extracellular matrix comprising collagen, fibronectin and/or laminin.

13. The device of claim 11, wherein the biocompatible material is selected from the group consisting of collagen, laminin, proteoglycan, vitronectin, fibronectin, poly-D-lysine and polysaccharide.

14. A method comprising:
providing an organomimetic device having a body, the body including an at least partially porous and at least partially flexible membrane positioned along a plane within a central microchannel to partition the central microchannel into a first central microchannel and a second central microchannel, the membrane coated with at least one attachment molecule that supports adhesion of a plurality of living cells, and at least one operating channel separated from the first and second central microchannels by a microchannel wall, wherein the membrane is fixed to the microchannel wall;
applying a first fluid through the first central microchannel;
applying a second fluid through the second central microchannel;
applying a pressure to the at least one operating channel to cause the membrane to flex in a desired direction to expand or contract along the plane within the first and second central microchannels; and
monitoring behavior of cells with respect to the membrane between the first and second central microchannels.

15. The method of claim 14, wherein the applying a pressure differential further comprises:
increasing the pressure such that one or more sides of the membrane move in desired directions along the plane; and
decreasing the pressure such that the one or more sides of the membrane move in an opposite direction along the plane.

16. A method for determining an effect of at least one agent in a tissue system with physiological or pathological mechanical force, the method comprising:
selecting a device having a body, the body including an at least partially porous and at least partially flexible membrane positioned along a plane within a central microchannel to partition the central microchannel into a first central microchannel and a second central microchannel, at least one operating channel separated from the first and second central microchannels by a microchannel wall, wherein the membrane is fixed to the microchannel wall;
contacting the membrane with at least one layer of cells on a first side of the membrane and at least one layer of cells on a second side of the porous membrane thereby forming a tissue structure comprising at least two different types of cells;
contacting the tissue structure comprising at least two different types of cells with the at least one agent in an applicable cell culture medium;
applying uniform or non-uniform force on the cells for a time period; and
measuring a response of the cells in the tissue structure comprising at least two different types of cells to determine the effect of the at least one agent on the cells.

17. The method of claim 16, wherein the uniform or non-uniform force is applied using vacuum.

18. The method of claim 16, wherein the tissue structure comprising at least two different types of cells comprises alveolar epithelial cells on the first side of the porous membrane and pulmonary microvascular cells on the second side of the porous membrane.

19. The method of claim 16, wherein the agent is selected from the group consisting of nanoparticles, environmental toxins or pollutant, cigarette smoke, chemicals or particles used in cosmetic products, drugs or drug candidates, aerosols, naturally occurring particles including pollen, chemical weapons, single or double-stranded nucleic acids, viruses, bacteria and unicellular organisms.

20. The method of claim 16, wherein the device further comprises:
a second operating channel separated from the first and second central microchannels by a second microchannel wall, wherein an opposing end of the membrane is mounted to the second microchannel wall, when a pressure is applied to the second operating channel, it causes the membrane to flex in a second desired direction to expand or contract along the plane within the first and second central microchannels.

21. The method of claim 14, wherein the device further comprises:
a second operating channel separated from the first and second central microchannels by a second microchannel wall, wherein an opposing end of the membrane is mounted to the second microchannel wall, when a pressure is applied to the second operating channel, it causes the membrane to flex in a second desired direction to expand or contract along the plane within the first and second central microchannels.

* * * * *

UNITED STATES PATENT AND TRADEMARK OFFICE
CERTIFICATE OF CORRECTION

PATENT NO. : 8,647,861 B2  Page 1 of 1
APPLICATION NO. : 13/054095
DATED : February 11, 2014
INVENTOR(S) : Ingber et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 124 days.

Signed and Sealed this
Twenty-ninth Day of September, 2015

Michelle K. Lee
*Director of the United States Patent and Trademark Office*